(12) United States Patent
Hall et al.

(10) Patent No.: US 12,268,619 B2
(45) Date of Patent: Apr. 8, 2025

(54) ENDOVASCULAR PROSTHESIS WITH SELECTIVELY OPENABLE INTERNAL DUCT

(71) Applicant: Merit Medical Systems, Inc., South Jordan, UT (US)

(72) Inventors: John Hall, Bountiful, UT (US); Christopher Cindrich, Highland, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 1143 days.

(21) Appl. No.: 17/070,242

(22) Filed: Oct. 14, 2020

(65) Prior Publication Data

US 2021/0106444 A1    Apr. 15, 2021

Related U.S. Application Data

(60) Provisional application No. 62/915,130, filed on Oct. 15, 2019.

(51) Int. Cl.
| | |
|---|---|
| *A61F 2/856* | (2013.01) |
| *A61F 2/07* | (2013.01) |
| *A61F 2/90* | (2013.01) |
| *A61F 2/95* | (2013.01) |

(52) U.S. Cl.
CPC ............... *A61F 2/856* (2013.01); *A61F 2/07* (2013.01); *A61F 2/90* (2013.01); *A61F 2/95* (2013.01); *A61F 2210/0076* (2013.01); *A61F 2250/0069* (2013.01)

(58) Field of Classification Search
CPC .... A61F 2/856; A61F 2/06; A61F 2/07; A61F 2/95; A61F 2002/061; A61F 2210/0076; A61F 2250/0069
See application file for complete search history.

(56) References Cited

U.S. PATENT DOCUMENTS

| | | | |
|---|---|---|---|
| 7,144,421 | B2 | 12/2006 | Carpenter et al. |
| 8,052,736 | B2 | 11/2011 | Doig et al. |
| 8,273,115 | B2 | 9/2012 | Hamer et al. |
| 8,394,136 | B2 | 3/2013 | Hartley et al. |

(Continued)

FOREIGN PATENT DOCUMENTS

| | | |
|---|---|---|
| WO | 199800090 | 1/1998 |
| WO | 2013040663 | 3/2013 |
| WO | 2018018114 | 2/2018 |

OTHER PUBLICATIONS

International Search Report and Written Opinion dated Feb. 4, 2021 for PCT/US2020/055562.

(Continued)

*Primary Examiner* — William H Matthews
(74) *Attorney, Agent, or Firm* — Dorsey & Whitney LLP

(57) ABSTRACT

Endovascular prostheses used to treat diseased blood vessels, such as arteries, are disclosed. In some embodiments, the endovascular prosthesis is configured to be implanted within the diseased blood vessels adjacent a diseased section. The endovascular prosthesis may include a selectively openable internal duct configured to sealingly receive an expandable endovascular prosthesis that extends into a side branch vessel of the diseased blood vessel.

9 Claims, 16 Drawing Sheets

(56) References Cited

U.S. PATENT DOCUMENTS

| | | | |
|---|---|---|---|
| 8,672,993 B2* | 3/2014 | Chuter | A61F 2/07 |
| | | | 623/1.13 |
| 8,795,349 B2 | 8/2014 | Huser et al. | |
| 9,101,456 B2* | 8/2015 | Hartley | A61F 2/856 |
| 9,314,328 B2 | 4/2016 | Dake et al. | |
| 9,861,505 B2 | 1/2018 | Khoury | |
| 10,201,413 B2 | 2/2019 | Shalev et al. | |
| 2006/0149351 A1* | 7/2006 | Smirthwaite | A61F 2/07 |
| | | | 623/1.13 |
| 2009/0012597 A1 | 1/2009 | Doig et al. | |
| 2012/0290069 A1 | 11/2012 | Ivancev et al. | |
| 2015/0127089 A1* | 5/2015 | Ducke | A61F 2/86 |
| | | | 623/1.35 |
| 2015/0230916 A1 | 8/2015 | Ivancev et al. | |
| 2017/0281332 A1 | 10/2017 | Lostetter | |
| 2018/0303598 A1 | 10/2018 | Szopinski et al. | |
| 2019/0151073 A1 | 5/2019 | Hartley | |
| 2019/0159886 A1 | 5/2019 | Lourenco | |

OTHER PUBLICATIONS

De La Cruz, et al.,Thoracoabdominal Aortic Aneurysm Repair with a Branched Graft, Ann Cardiothorac Surg, 1 (3) ,2012 ,381-393.
Extended European Search Report dated Oct. 9, 2023 for EP20876491.0.

* cited by examiner

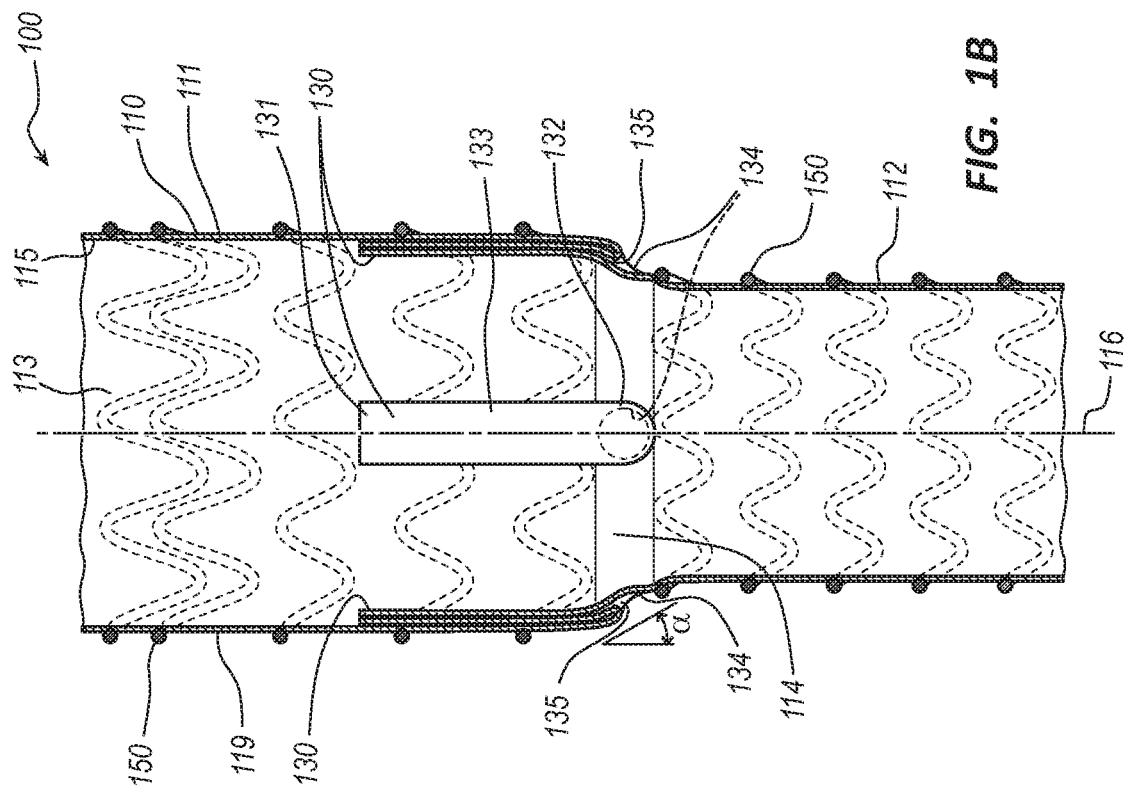
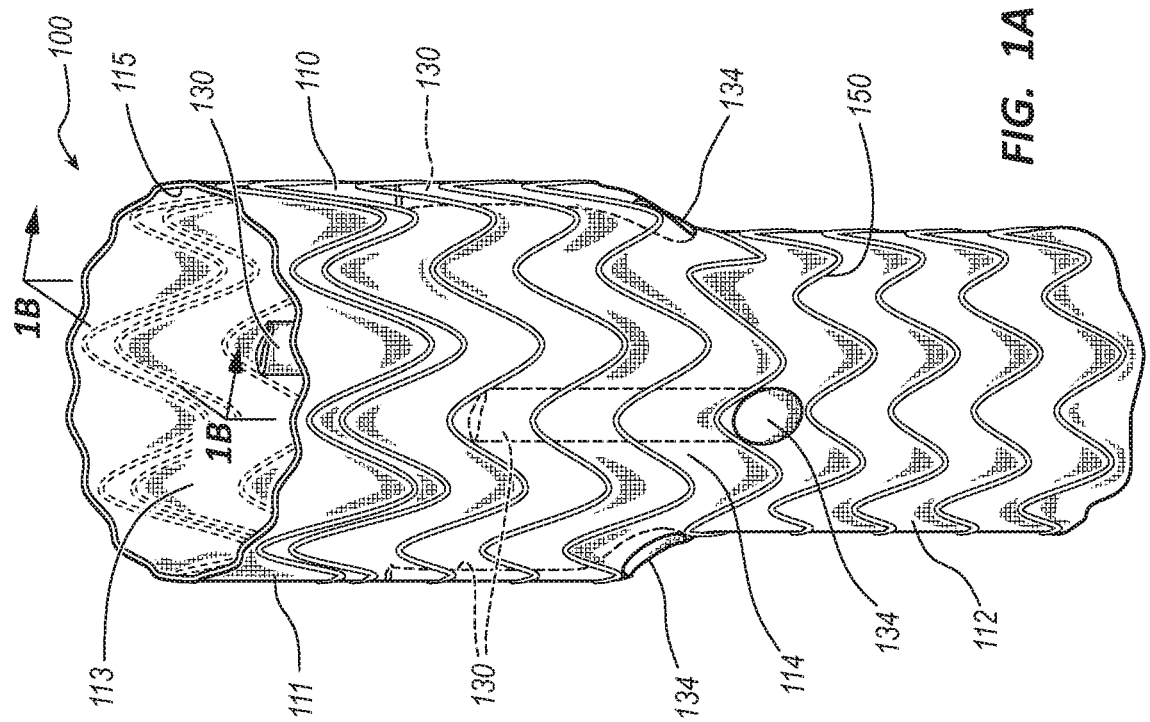
FIG. 1B
FIG. 1A

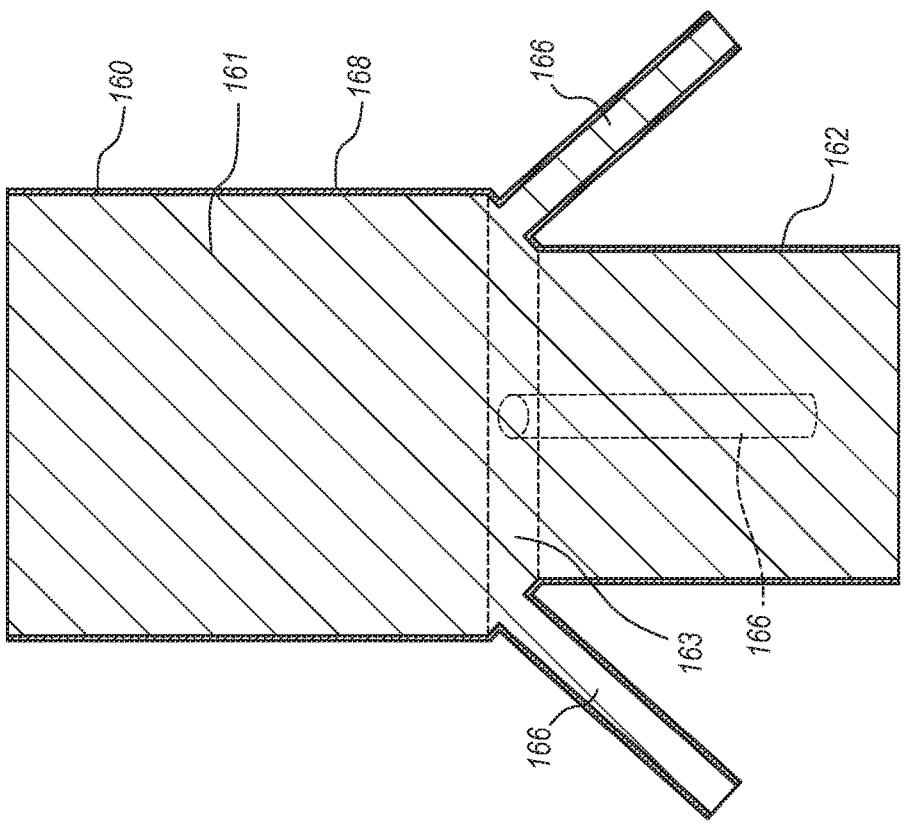
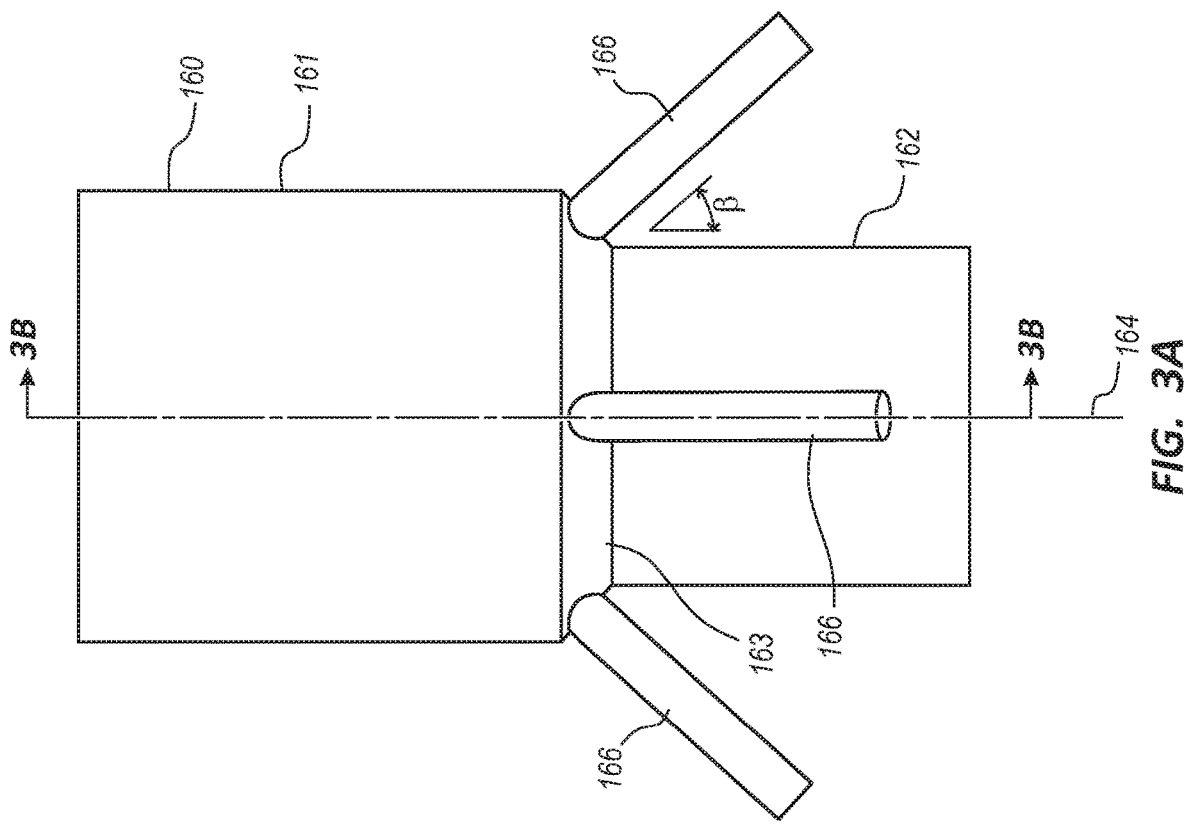
FIG. 3A
FIG. 3B

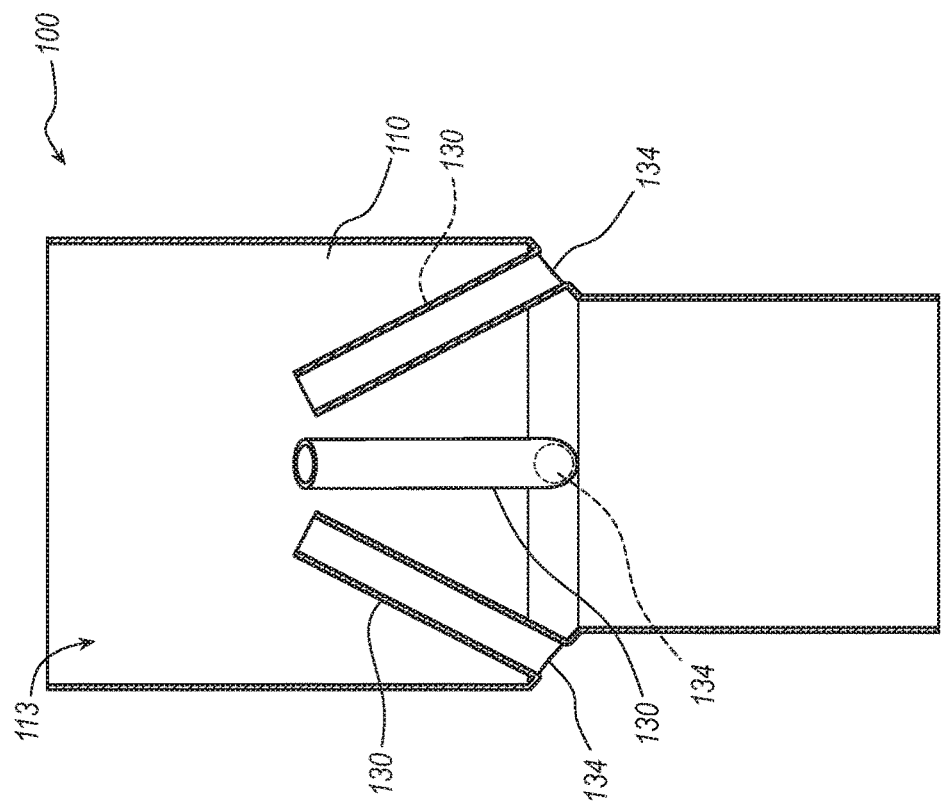
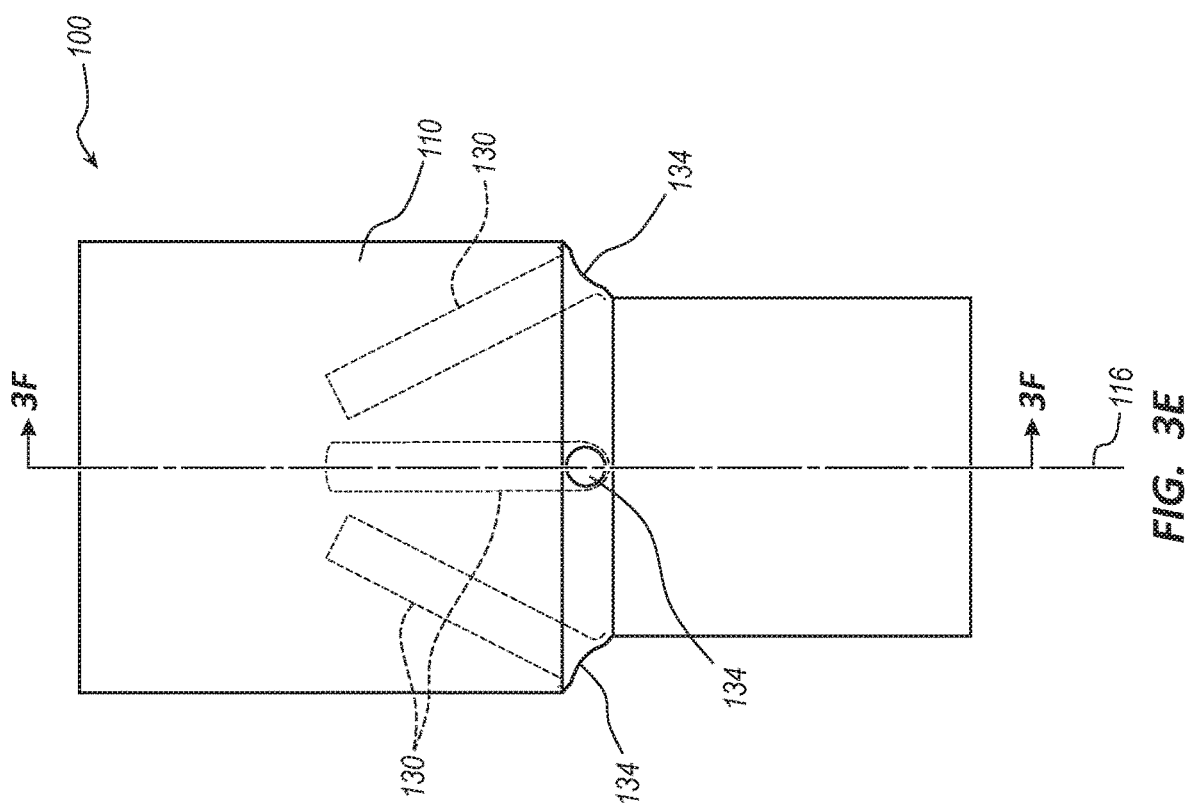
FIG. 3F
FIG. 3E

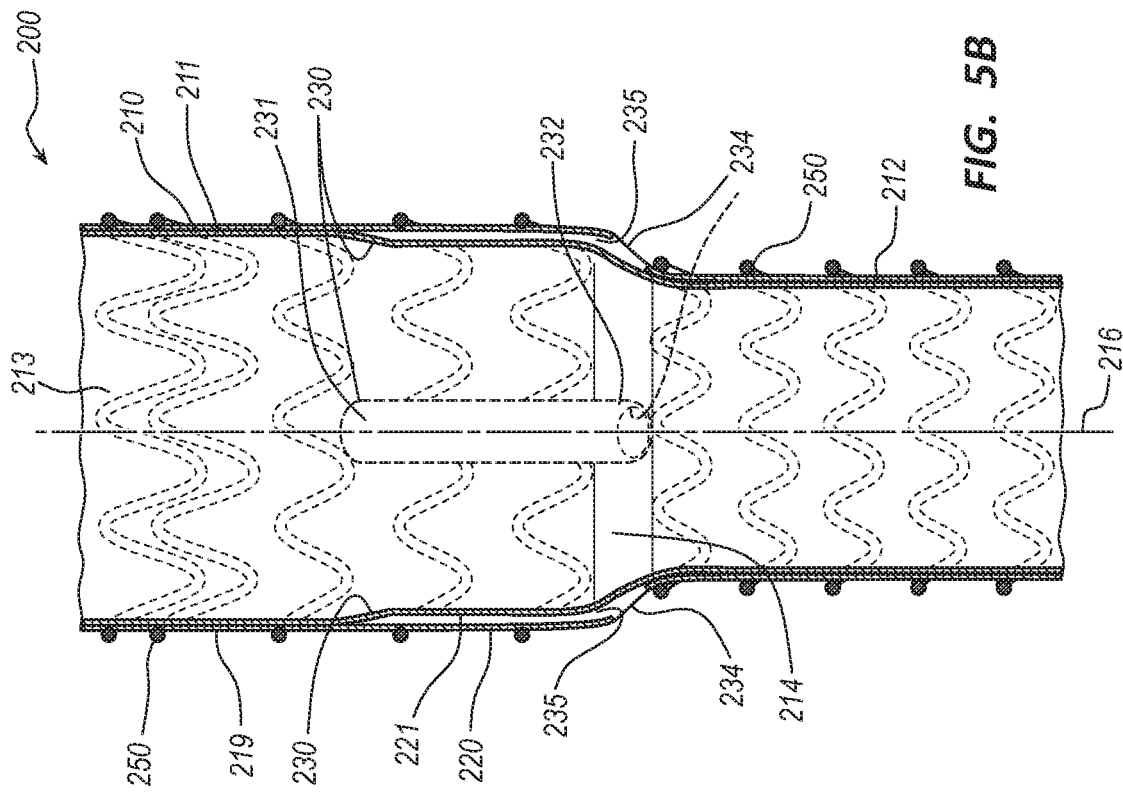
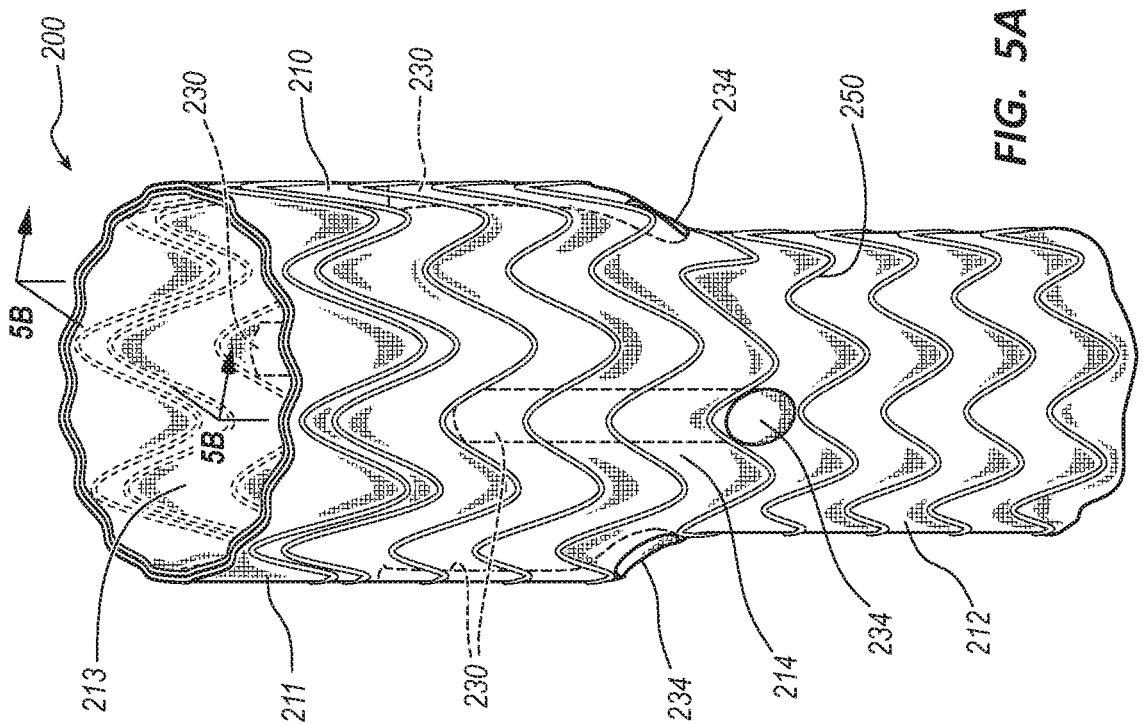

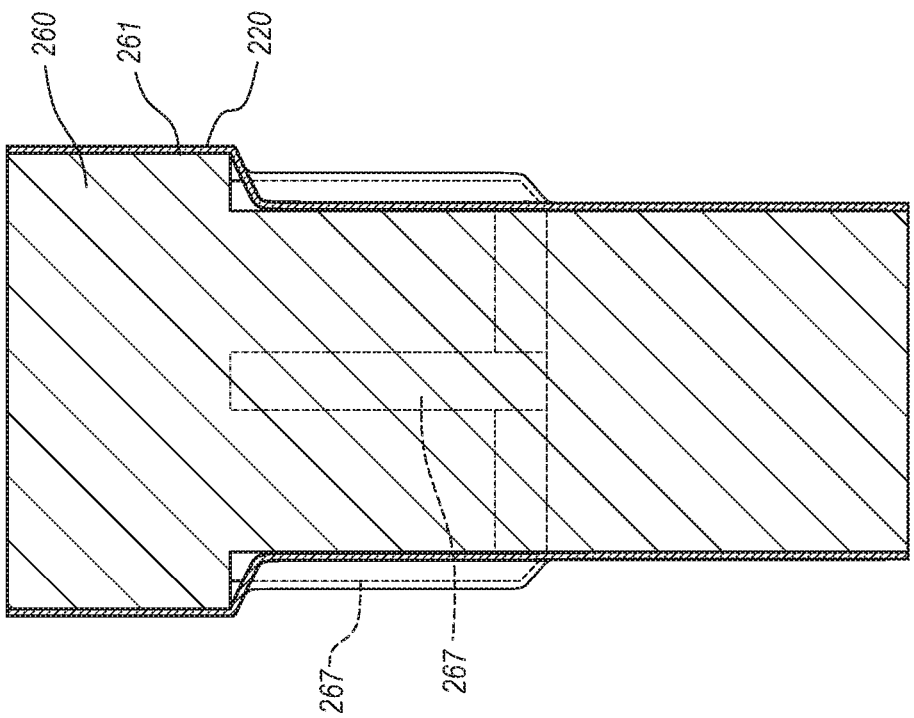
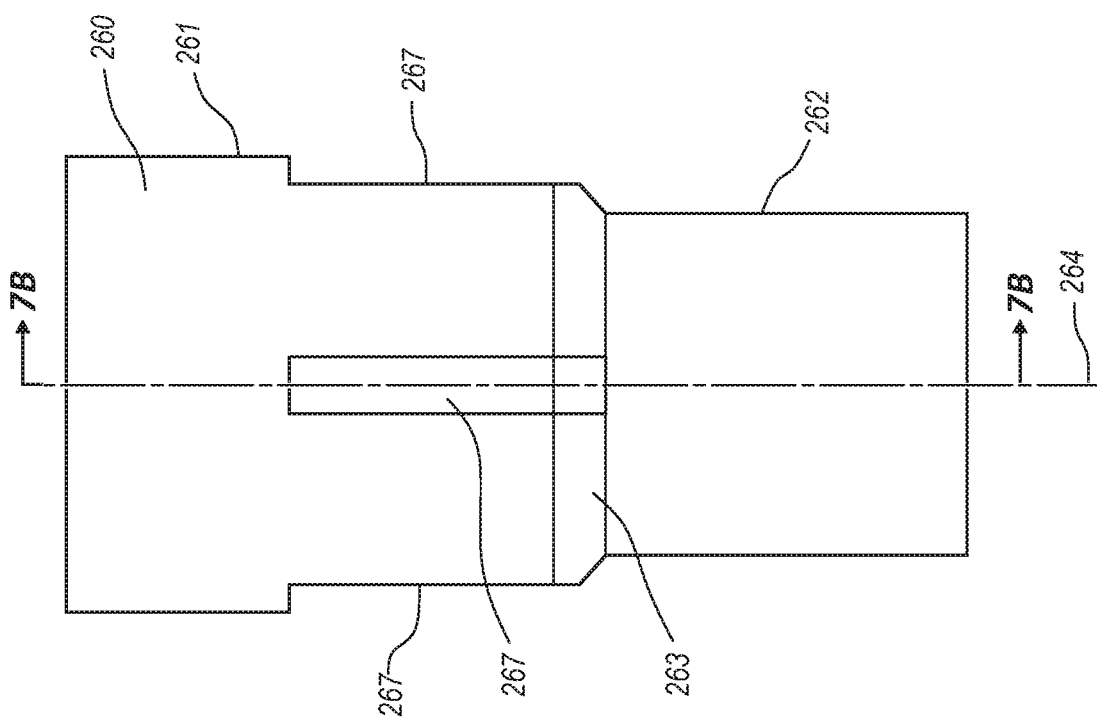

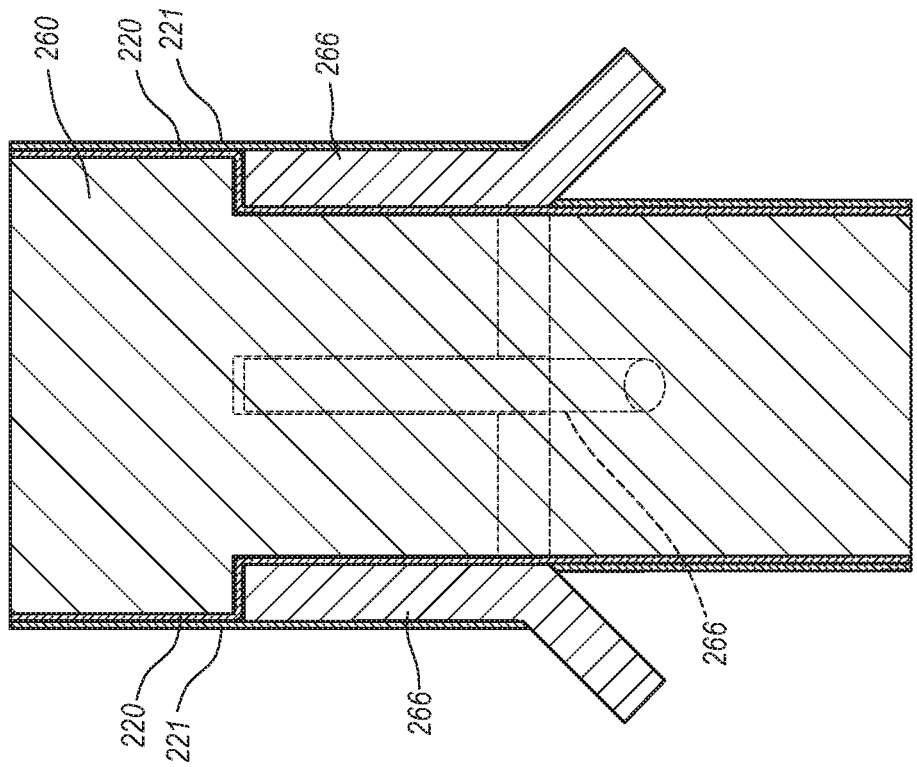
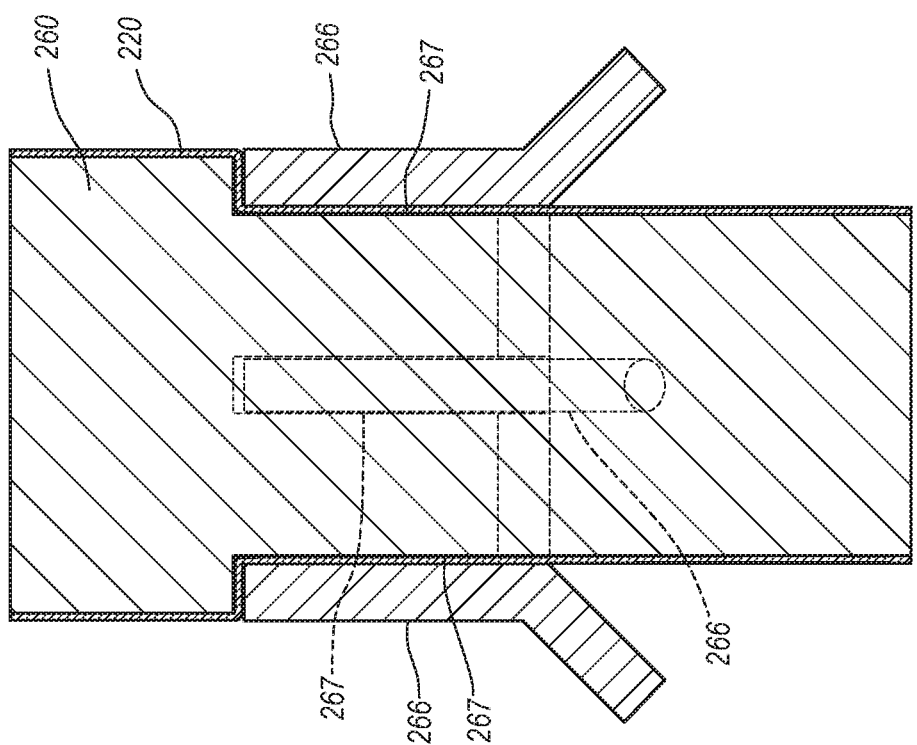
FIG. 7C
FIG. 7D

ENDOVASCULAR PROSTHESIS WITH SELECTIVELY OPENABLE INTERNAL DUCT

RELATED APPLICATION

This application claims priority to U.S. Provisional Application No. 62/915,130, filed on Oct. 15, 2019 and titled "Endovascular Prosthesis With Selectively Openable Internal Duct" which is hereby incorporated by reference in its entirety.

TECHNICAL FIELD

The present disclosure relates to an endovascular prosthesis. In some embodiments, the present disclosure relates to an endovascular prosthesis that provides access to branch arteries when implanted in a major artery, such as the aorta. Methods of manufacture and use of prosthesis are also disclosed.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a perspective view of an embodiment of an endovascular prosthesis.

FIG. 1B is a longitudinal cross-sectional view of the endovascular prosthesis of FIG. 1A.

FIG. 3A is a side view of an endovascular prosthesis forming mandrel.

FIG. 3B is a side view of the endovascular prosthesis forming mandrel of FIG. 3A covered with a material.

FIG. 3E is a side view of the tubular body of the endovascular prosthesis of FIG. 1A in a fully inverted state.

FIG. 3F is a longitudinal cross-sectional view of the tubular body of the endovascular prosthesis of FIG. 1A in a fully inverted state.

FIG. 5A is a perspective view of an embodiment of an endovascular prosthesis.

FIG. 5B is a longitudinal cross-sectional view of the endovascular prosthesis of FIG. 5A.

FIG. 7A is a side view of an endovascular prosthesis forming mandrel.

FIG. 7B is a cross-sectional view of the endovascular prosthesis forming mandrel of FIG. 7A covered with a first layer of material.

FIG. 7C is a cross-sectional view of the endovascular prosthesis forming mandrel of FIG. 7A with duct forming mandrels.

FIG. 7D is a cross-sectional view of the endovascular prosthesis forming mandrel of FIG. 7A with duct forming mandrels and covered by a second layer of material.

DETAILED DESCRIPTION

Figure 2B:
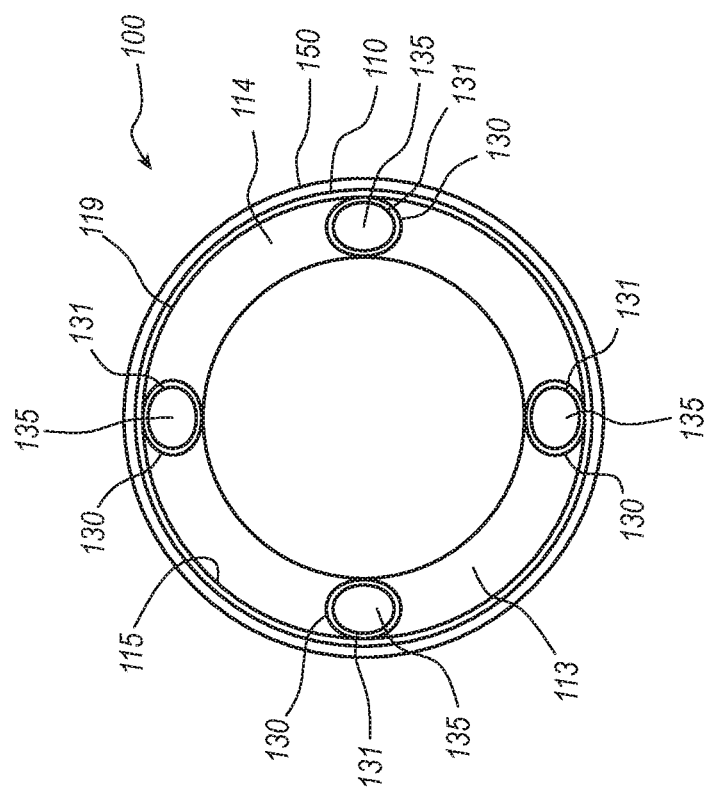
FIG. 2B is a top view of the endovascular prosthesis of FIG. 1A with ducts in an opened configuration.
Figure 2A:
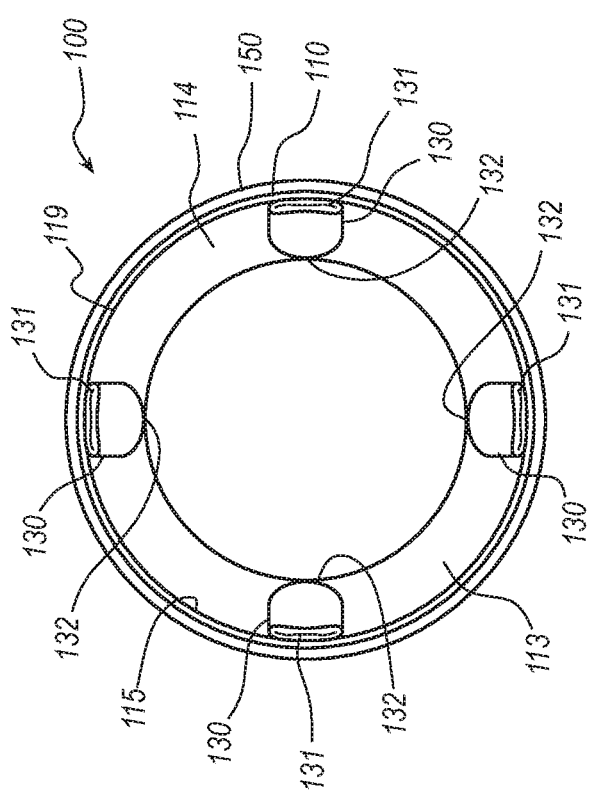
FIG. 2A is a top view of the endovascular prosthesis of FIG. 1A with ducts in a closed configuration.

Degenerative diseases of the arteries of a human body, such as aneurysms and dissections, may be treated by arterial replacement. Conventional open surgery for arterial replacement may be associated with significant risk of death or disability and may be especially dangerous for the vascular patient who typically has significant pre-existing surgical risk factors.

Minimally invasive alternatives to open vascular surgery have been developed, including processes whereby arterial replacement is performed by placement of an endovascular prosthesis via a remote access point. Such endovascular prostheses may be composed of an impervious fabric through which blood flows, preventing blood leakage though the prosthesis and directing blood flow through a portion of diseased arterial wall. The fabric may be sealed to a disease-free arterial wall above and below the diseased segment of artery to be bypassed. Such endovascular prostheses may be utilized to repair disease of the thoracic and abdominal aortas as well as peripheral arteries. Tubular prostheses may be limited in their inability to repair branched arteries, as a sealed tubular construct positioned across the opening of a branch artery would prevent blood flow to the branch artery. Examples of regions of the aorta which may be affected by arterial disease that include branches include the aortic arch, from which the innominate, carotid, and subclavian arteries originate, and the proximal abdominal aorta, from which the visceral and renal arteries emerge as side branches.

An endovascular prosthesis used to repair a section of the aorta having branch arteries may include a tubular body having a bore, a proximal portion configured to couple with healthy arterial tissue, and a tapered portion. At least one duct may extend into the bore from the tapered portion. The duct may include an opening at a distal end that is in fluid communication with a lumen of the duct. The opening may be disposed adjacent the tapered portion. The duct may be selectively openable and, in some embodiments, may be configured in a closed configuration until opened by a clinician during a repair procedure. The opened duct may be configured to sealingly receive an endovascular prosthesis that extends through the duct and into a branch vessel.

A method of manufacturing an endovascular prosthesis may include obtaining a body forming mandrel for forming the body of the endovascular prosthesis. The body forming mandrel may include at least one duct forming mandrel extending radially outward from the body forming mandrel. The duct forming mandrel may be disposed at a tapered portion of the body forming mandrel. The body forming mandrel and the duct forming mandrel may be covered, such as with a biocompatible material, to form the body of the endovascular prosthesis and at least one duct. The body and duct may be removed from the body forming mandrel and the duct forming mandrel and inverted such that an inside surface becomes an outside surface and the duct is disposed inside the bore of the body. In some embodiments, the duct may be closed and coupled to the wall of the body.

A method of repairing a diseased portion of the aorta having a branch artery may include deploying the endovascular prosthesis into the aorta such that the proximal portion of the endovascular prosthesis is in contact with healthy tissue, opening a duct of the endovascular prosthesis with an elongate instrument such as a guidewire, and deploying a stent graft through the opened duct and into the branch artery. Deployment and treatment of other vessels or regions of the vasculature are likewise within the scope of this disclosure.

Embodiments may be understood by reference to the drawings, wherein like parts are designated by like numerals throughout. It will be understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of an implanted medical device means the end of the device furthest from the heart. The proximal end refers to the opposite end, or the end nearest the heart. As specifically applied to an endovascular prosthesis, the proximal end of the prosthesis refers to the end configured for deployment nearest the heart (along the blood flow path of the vasculature) and the distal end refers to the opposite end, the end farthest from the heart. If at one or more points in a procedure a physician changes the orientation of the prosthesis, as used herein, the term "proximal end" always refers to the end configured for deployment closest to the heart when implanted.

FIGS. 1A-7H illustrate various views of an endovascular prosthesis and related components. In certain views each endovascular prosthesis may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1A-2B depict an embodiment of an endovascular prosthesis 100. In the illustrated embodiment, the endovascular prosthesis 100 is partially composed of a tubular body 110 and a wire scaffold, framework, or stent, such as wire stent 150. The tubular body 110 may be generally cylindrical in shape having a proximal portion 111, a distal portion 112, a tapered portion 114, and a bore 113. The tubular body 110 may be formed of a variety of materials and/or layers of materials, including biocompatible materials that are resistant to passage of blood and/or cells through a wall 119 of the tubular body 110. For example, the tubular body 110 may be formed of polyethylene terephthalate, polyurethane, silicone rubber, nylon, fluoropolymer, polyester, etc. A thickness of the wall 119 may range from about 0.07 mm to about 0.5 mm.

In some embodiments, a length of the tubular body 110 may range from about 50 mm to about 250 mm with a length of the proximal portion 111 ranging from about 20% to about 80% of the length of the tubular body 110. An outer diameter of the proximal portion 111 may be larger than an outer diameter of the distal portion 112 and may range from about 18 mm to about 55 mm. An outer diameter of the distal portion 112 may range from about 18 mm to about 55 mm. The tapered portion 114 may have a taper angle $\alpha$ relative to a longitudinal axis 116 of the tubular body 110 ranging from about 10 degrees to about 60 degrees. In other embodiments, the tubular body 110 may be a substantially straight cylinder having a constant outer diameter dimension. In still other embodiments, the tubular body 110 may be tapered over the length of the tubular body 110 where the taper angle ranges from about two degrees to about 15 degrees. In one embodiment, the tubular body 110 may include a flared proximal end to facilitate sealing of the proximal portion 111 with a vessel wall and to prevent leakage of blood between the proximal portion 111 and the vessel wall. In some embodiments, the tubular body 110 may include a cuff disposed adjacent the proximal portion 111 configured to facilitate sealing of the proximal portion 111 with the vessel wall and to prevent leakage of blood between the proximal portion 111 and the vessel wall. In other embodiments, the tubular body 110 may include fixation features configured to prevent migration of the endovascular prosthesis 100 relative to the vessel wall. The fixation features may include protruding barbs, sharpened protruding barbs, an adhesive, inflatable portions, etc.

In the illustrated embodiment, the tubular body 110 includes a plurality of ducts 130. In various embodiments, the tubular body 110 may include one, two, three, four, or more ducts 130. The tubular body 110 and the duct 130 may be formed to be an integral or unibody component such that there is not a seam or joint at a junction of the tubular body 110 and the duct 130. The duct 130 includes a proximal end 131, a distal end 132, a middle portion 133, a distal opening 134, and a lumen 135. The duct 130 may be cylindrical in shape and formed from any of the materials listed for forming the tubular body 110. In other embodiments, the duct 130 may include any suitable transverse cross-sectional shape, such as oval, obround, semicircular, D-shaped, etc. In some embodiments, the duct 130 may be formed of the same material as the tubular body 110 while in other embodiments these elements may be formed of different materials. A length of the duct 130 may range from about 5 mm to about 50 mm. In some embodiments, the lengths of the ducts 130 are approximately equivalent. In other embodiments, the lengths of the plurality of ducts 130 may be different from one duct 130 to another duct 130. The proximal ends 131 of the ducts 130 may be disposed from adjacent a proximal end of the tubular body 110 to adjacent the distal opening 134 of the duct 130. An internal diameter of the ducts 130 may be configured to receive an expandable vascular prosthesis. For example, a diameter of the lumen 135 may range from about 2 mm to about 30 mm. A thickness of a wall of the duct 130 may range from about 0.07 mm to about 0.5 mm.

In certain embodiments, the wall 119 of the tubular body 110 and/or the wall of the duct 130 may be impermeable to tissue cell ingrowth into and/or tissue cell migration through the wall 119 and the wall of the duct 130, for example, to prevent or discourage stenosis of the tubular body 110 and/or the duct 130. Additionally or alternatively, in some embodiments, the wall 119 of the tubular body 110 and/or the wall of the duct 130 can be impermeable to blood such that blood is prevented from leaking from the inside of the endovascular prosthesis 100 to the exterior of the endovascular prosthesis 100 and into surrounding tissue. Still further, in some embodiments an interior surface of the wall 119 and/or an interior surface of the wall of the duct 130 may include serially deposited fibers of polytetrafluoroethylene (PTFE) to resist fibrin deposition and platelet adhesion on the surfaces.

In the illustrated embodiment, the distal opening 134 of each the duct 130 of the plurality of ducts 130 is disposed on the tapered portion 114. Positioning the distal opening 134 of any one, or all, of the ducts 130 along other portions of the tubular body 110 is also within the scope of this disclosure. In the illustrated embodiment, the distal opening 134 of each duct 130 is in fluid communication with the lumen 135 of the corresponding duct 130 and with an exterior environment of the endovascular prosthesis 100. In some embodiments, the distal openings 134 of the ducts 130 may be spaced equidistance around a circumference of the tapered portion 114. In other embodiments, the distal openings 134 may be spaced with a variable distance between the distal openings 134. Such spacing may be related to or dependent on an orientation of branch arteries along a treatment area. In another embodiment, the distal openings may be disposed at any suitable location within the proximal portion 111, distal portion 112, and tapered portion 114 of the tubular body 110.

In the illustrated embodiment, for each duct 130, the distal opening 134 is in fluid communication with the corresponding lumen 135. The lumen 135 extends from the distal opening 134 to the proximal end 131 of the lumen 135. Each lumen 135 and distal opening 134 may be configured to be selectively disposed in a closed configuration or an opened configuration. The lumens 135 and the proximal ends 131 for each duct 130 are shown in closed configurations in FIGS. 1A, 1B, and 2A and in opened configurations in FIG. 2B. As detailed below, during use some of the lumens 135 may be disposed in the opened configuration while others are in the closed configuration.

For each duct 130 and lumen 135 of the illustrated embodiment, in the closed configuration the proximal end 131 and the lumen 135 are selectively closed. The proximal end 131 may be selectively closed by application of an adhesive, such as fluorinated ethylene propylene (FEP), polyurethane, silicone, etc. or any other suitable adhesive material. In other embodiments, a flexible member, such as a ring, may be coupled to the proximal end 131 to allow the proximal end 131 to be selectively opened. In another embodiment, the proximal end 131 may be closed using any suitable technique, such as heat sealing, radio frequency welding, ultrasound welding, etc. In the closed configuration the duct 130 may be radially compressed against the wall 119 of the tubular body 110 such that the duct 130 may not extend into the bore 113 or such that the duct 130 assumes a low-profile configuration along the wall 119 of the tubular body 110. In the opened configuration, the duct 130 may extend into the bore 113 and allow blood to flow through the duct 130.

In the illustrated embodiment, each duct 130 may be oriented such that it extends in a proximal direction along the wall 119 of the bore 113. In another embodiment, each duct 130 may be oriented in a distal direction. In still another embodiment, a portion of the ducts 130 may be oriented in the proximal direction and a portion of the ducts 130 may be oriented in the distal direction. A portion of the duct 130, such as a middle portion 133, may be coupled to the wall 119 using an adhesive, such as FEP, polyurethane, silicone, etc. or any other suitable adhesive. In other embodiments, the duct 130 may be coupled to the wall 119 using a suture stitch. Further, in other embodiments, the duct 130 may be coupled to the wall 119 using clips or staples. In another embodiment, the duct 130 may be fully integrally formed within the wall 119 of the tubular body 110. In yet other embodiments, the duct 130 may be partially integrally formed within the wall 119.

The wire scaffolding, framework, or stent such as wire stent 150 is shown to circumferentially surround the tubular body 110. The wire stent 150 may be configured to radially expand the tubular body 110 from a crimped or delivery configuration to a deployed configuration. When the endovascular prosthesis 100 is deployed within a blood vessel, the tubular body 110 may be pressed against a wall of the blood vessel. The wire stent 150 may be formed of any suitable material, such as nickel-titanium alloy, stainless steel, platinum, polymers, etc. The wire stent 150 may have a zig-zag pattern, a wave pattern, or any other suitable pattern. The wire stent 150 may be pre-formed or formed over the tubular body 110. The material, pattern, and wire diameter of the wire stent 150 may be configured to provide a chronic radial outwardly directed force and a resistance to a radial inwardly directed force.

Figures 3C, 3D:
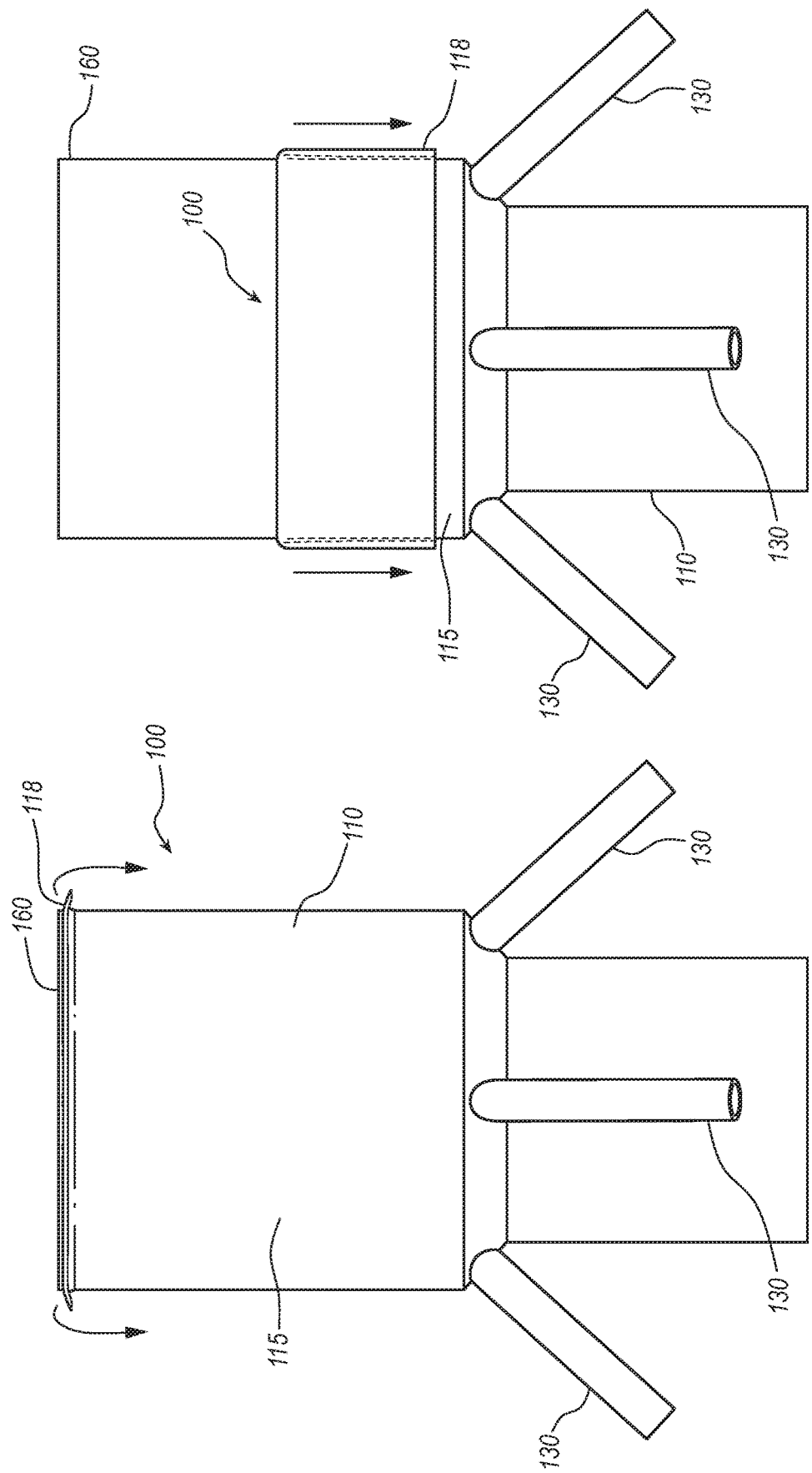
FIG. 3C is a side view of the endovascular prosthesis forming mandrel of FIG. 3A with a tubular body of the endovascular prosthesis of FIG. 1A in a pre-inverted state.
FIG. 3D is a side view of the endovascular prosthesis forming mandrel of FIG. 3A with the tubular body of the endovascular prosthesis of FIG. 1A in a partial inverted state.

FIGS. 3A-3H illustrate a method of manufacturing the endovascular prosthesis 100. FIG. 3A depicts a body forming mandrel 160. The body forming mandrel 160 may include a proximal portion 161, a distal portion 162, a tapered portion 163, and a plurality of duct forming mandrels 166. The body forming mandrel 160 may be generally cylindrical in shape and formed from any suitable material, such as stainless steel, aluminum, etc. As depicted in FIG. 3B, the body forming mandrel 160 may have a solid transverse cross-section. In other embodiments, the body forming mandrel 160 may include a bore extending through the body forming mandrel 160. The dimensions (e.g., lengths, diameters, angle) of the body forming mandrel 160 may correspond to the dimensions of the tubular body 110 previously described.

In various embodiments, the body forming mandrel 160 may include one, two, three, four, or more duct forming mandrels 166. In the illustrated embodiment, each duct forming mandrel 166 is shown to extend radially outward from the body forming mandrel 160 at an angle β relative to the longitudinal axis 164 of the body forming mandrel 160 which may be approximately equivalent to the angle α of the duct 130 of the tubular body 110. Embodiments wherein different duct forming mandrels 166 are disposed at different angles from each other (thus configured to create ducts 130 disposed at different angles) are likewise within the scope of this disclosure. The diameter and length dimensions of each duct forming mandrel 166 may be approximately equivalent to the dimensions of the ducts 130 previously described. The duct forming mandrels 166 may be formed from the same material as the body forming mandrel 160 or may comprise other materials. The duct forming mandrels 166 may be coupled to the body forming mandrel 160 using any suitable technique, such as bonding, gluing, welding, friction fit, press fit, machining, threading, etc. In some embodiments, the duct forming mandrels 166 may be permanently coupled to the body forming mandrel 160. In other embodiments, the duct forming mandrels 166 may be releasably coupled to the body forming mandrel 160 to facilitate removal of the tubular body 110 from the mandrels 160, 166 as will be discussed below. In certain embodiments, the duct forming mandrels 166 may be a flat strip formed from a film, such as a polyimide or metal film.

FIG. 3B depicts the body forming mandrel 160 and the duct forming mandrels 166 covered with a material layer 168 to form the tubular body 110 such that the tubular body 110 that is formed is a unibody or integral structure. In other words, in some embodiments, the tubular body 110 formed by the disclosed method does not have any seams between the tubular body 110 and the ducts 130. The material layer 168 may be comprised of any of the materials of the tubular body 110 discussed above. The material layer 168 may be applied using any suitable technique. For example, the material layer 168 may be applied by wrapping strips of material around the body forming mandrel 160 and the duct forming mandrel 166, dipping the body forming mandrel 160 and the duct forming mandrel 166 into a material solution, spraying the body forming mandrel 160 and the duct forming mandrel 166 with the material solution, etc. In some embodiments, the material layer 168 may include multiple sub-layers of either the same material or different materials. The material layer 168 may be cured and/or sintered prior to removal from the body forming mandrel 160 and the duct forming mandrel 166. The curing and/or sintering parameters may include heat, moisture, ultraviolet radiation, etc. and may be dependent upon the material of the material layer 168.

FIG. 3C shows the tubular body 110 in a pre-inverted state prior to the tubular body 110 being removed from the body forming mandrel 160 and the duct forming mandrels 166. As shown in FIG. 3C, the material which will form the interior surface 115 of the tubular body 110 is on the outside and the material which will form the exterior surface 118 of the tubular body 110 is in contact with the body forming mandrel 160. The ducts 130 are extending radially outward from the tubular body 110. In other words, the material layer 168 may be applied to the body forming mandrel 160 and duct forming mandrels 166 with the material layer 168 being inverted after application to form the vascular prosthesis 100.

FIG. 3D shows the tubular body 110 of FIG. 3C partially removed from the mandrel 160 and partially inverted such that a portion of the interior surface 115 is on the inside of the tubular body 110 and a portion of the exterior surface 118 is on the outside of the tubular body 110.

FIGS. 3E and 3F depict the tubular body 110 fully inverted where the ducts 130 are inverted and disposed on the inside of the tubular body 110 and the distal openings 134 of the ducts 130 are disposed on the outside of the tubular body 110. The interior surface 115 is on the inside and the exterior surface 118 is on the outside of the tubular body 110.

Figure 3H:
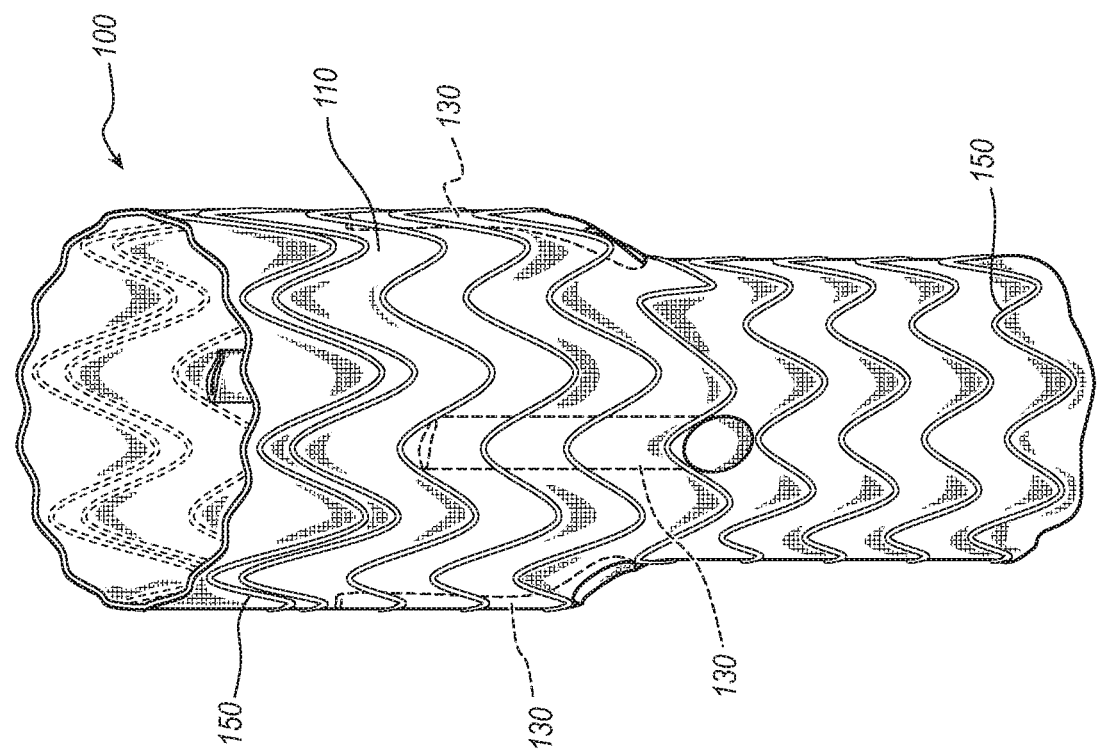
FIG. 3H is another perspective view of the endovascular prosthesis of FIG. 1A.
Figure 3G:
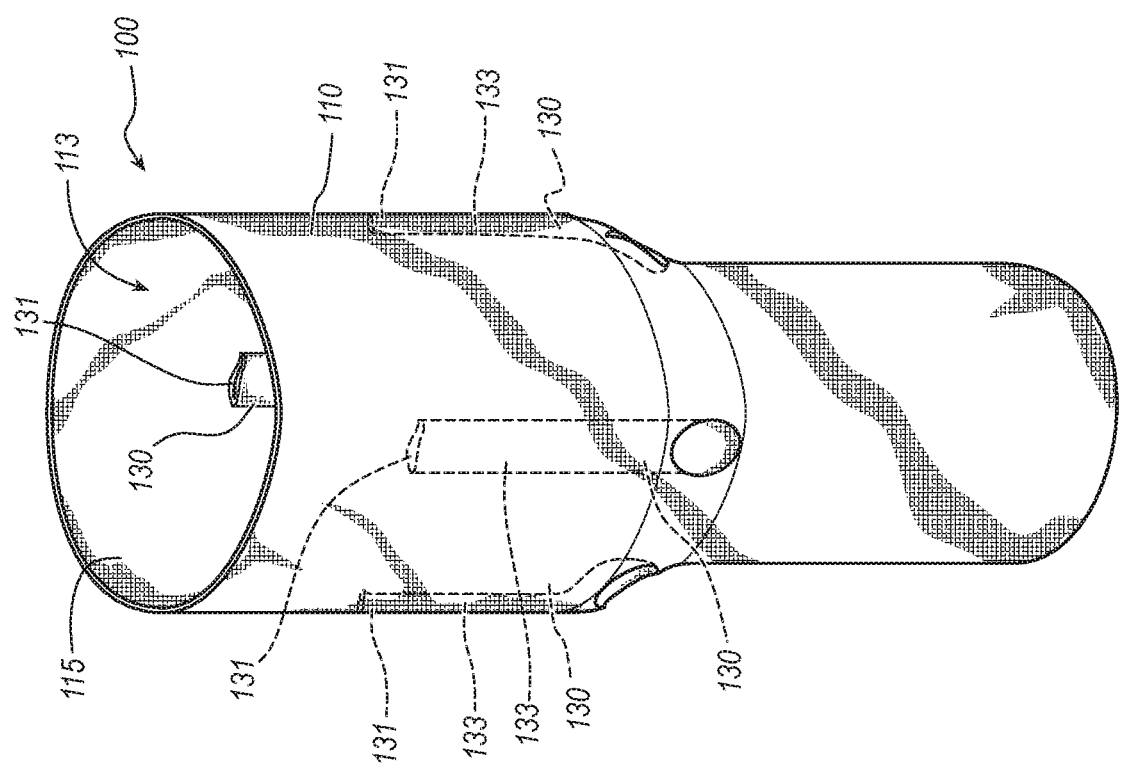
FIG. 3G is a perspective view of the tubular body of the endovascular prosthesis of FIG. 1A with ducts in the closed configuration.

FIG. 3G illustrates the tubular body 110 with the portion of the duct 130 coupled to the interior surface 115 of the bore 113. The duct 130 may be radially compressed against the interior surface 115. The middle portion 133 may be coupled to the interior surface 115 using any suitable technique, such as using an adhesive, suture stitches, clips, staples, etc. FIG. 3G also shows the proximal end 131 of the duct 130 in the closed configuration. The proximal end 131 may be closed using any suitable technique that will allow the proximal end 131 to be selectively openable. For example, the proximal end 131 may be closed by applying an adhesive, welding, crimping, etc. The adhesive that may be applied to the proximal end 131 may include any suitable adhesive, such as FEP, polyurethane, silicone, etc. In another embodiment, a flexible member may be coupled to the proximal end 131. In still another embodiment, the proximal end 131 may be treated with a laser to provide indents, perforations, areas of weakness, etc. such that the closed proximal end 131 could tear at a desired location.

FIG. 3H shows the wire stent 150 surrounding and coupled to the tubular body 110 to complete the manufacturing of the endovascular prosthesis 100. The wire stent 150 may be applied around the tubular body 110 after the tubular body is removed from the mandrel 160 and inverted. The wire stent 150 may be pre-formed on a wire bending mandrel prior to placement over the tubular body 110. In another embodiment, the wire stent 150 may be wound around the tubular body 110. The wire stent 150 may be coupled to the tubular body 110 using any suitable technique. For example, the wire stent 150 may be coupled to the tubular body 110 using an adhesive, suture stitches, clips, staples, tapes, films, membranes, etc. In some embodiments, the wire stent 150 may be captured between layers of the materials of the tubular body 110. For example, a first layer of material can be applied to the body forming mandrel 160, the wire stent 150 positioned over the first layer, and then a second layer of material applied over the wire stent 150.

Figure 4A:
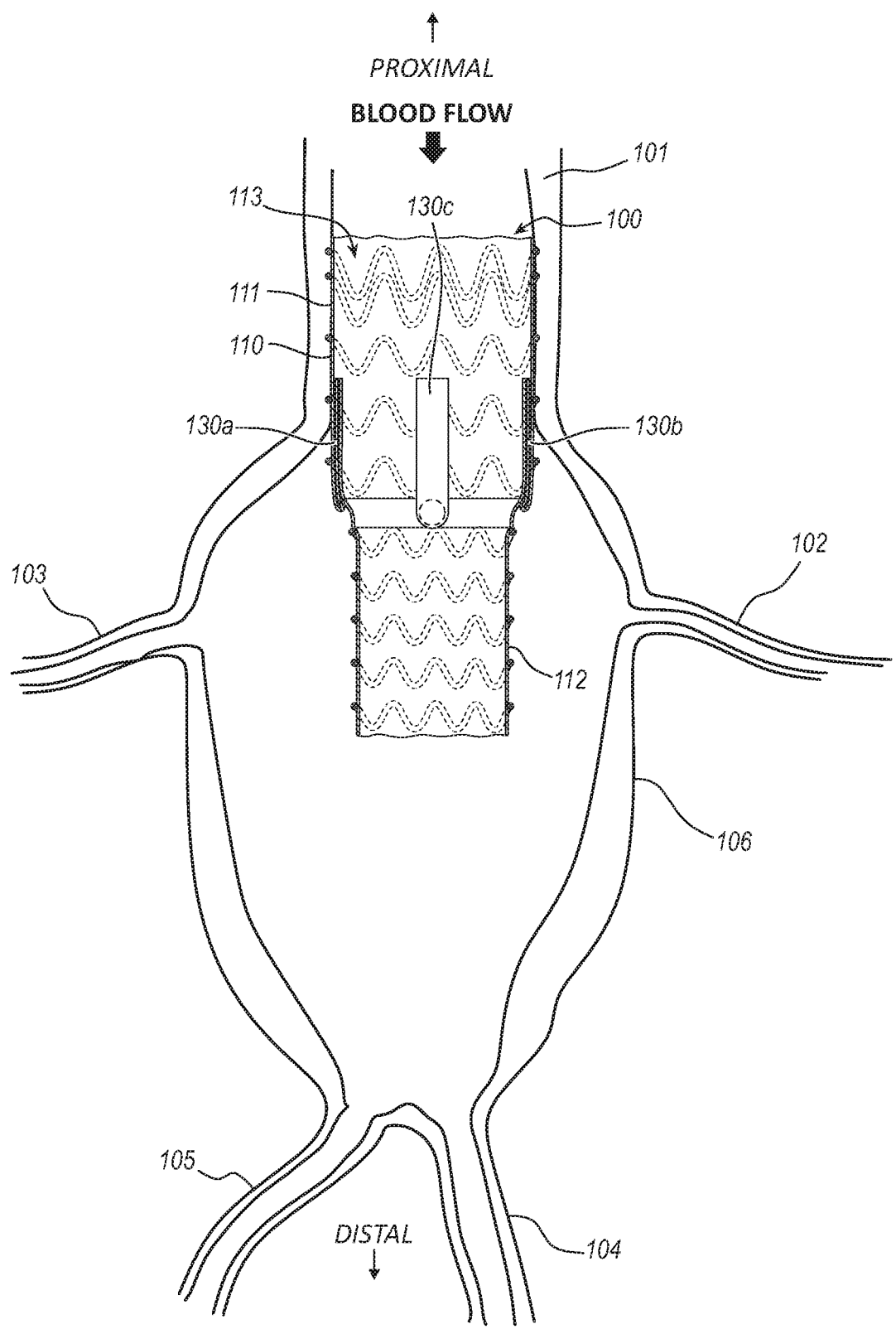
FIG. 4A is a side cross-sectional view of the endovascular prosthesis of FIG. 1A implanted in a vessel.

FIGS. 4A-4D illustrate a method of implanting the endovascular prosthesis 100 in a diseased blood vessel having branch vessels. FIG. 4A shows the endovascular prosthesis 100 deployed in a vessel 101. The endovascular prosthesis 100 may be deployed in any diseased arterial or venous vessel having branches, such as an aortic arch, a thoracic aorta, an abdominal aorta, inferior vena cava, etc. The tubular body 110 may be radially expanded to compress the proximal portion 111 against a healthy tissue section of a wall of the vessel 101 proximal to a diseased section 106 of the vessel 101 such that the endovascular prosthesis 100 may be secured in place. The distal portion 112 may extend distally into the diseased section 106 of the vessel 101. The diseased section 106 may be an aneurysm, an aortic dissection, or any other type of vascular disease. Vessel side branches 102, 103, such as the renal arteries, may extend radially outward from the diseased section 106. In other embodiments, the branch vessels 102, 103 may include a brachiocephalic trunk, left common carotid artery, left subclavian artery, bronchial arteries, esophageal arteries, intercostal arteries, mediastinal arteries, pericardial arteries, mesenteric arteries, gonadal arteries, lumbar arteries, etc. Upon initial deployment of the endovascular prosthesis 100, the ducts 130*a, b, c* may be disposed in a closed configuration such that blood flows through the bore 113 but does not flow through the ducts 130*a, b, c*. While three ducts 130*a*, 130*b*, 130*c* of the plurality of ducts (130 of FIG. 1A) are called out in these figures, the steps of deploying and implanting the endovascular prosthesis could be applied to a prosthesis with more or fewer ducts.

Figure 4B:
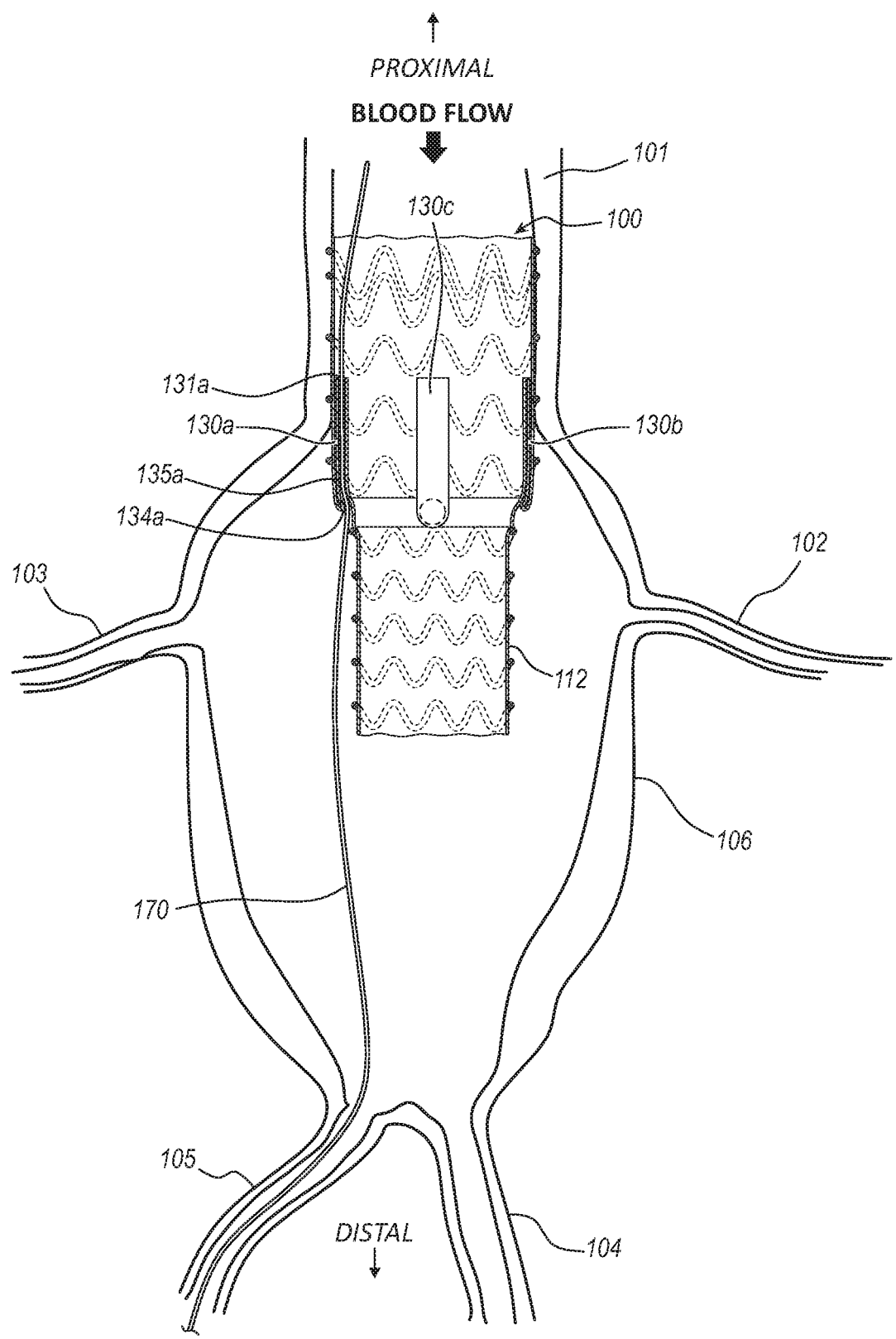
FIG. 4B is a side cross-sectional view of the endovascular prosthesis of FIG. 1A with an elongate medical device extending through a duct.

FIG. 4B shows an elongate medical instrument 170, such as a guidewire or a catheter, disposed within duct 130*a*. In some embodiments, elongate medical instruments, such as guidewires, may be partially disposed within each duct 130*a*, 130*b*, 130*c* of an endovascular prosthesis prior to deployment within the vasculature. For example, an endovascular prothesis 100 may be crimped into a deployment device with guidewires extending partially into each duct (130 of FIG. 1A) during manufacturing and loading of the endovascular prosthesis into a deployment device. Thus, the guidewires may be part of an endovascular prosthesis assembly when it is deployed into the vasculature, with the guidewires extending from a position partially inside each duct (130 of FIG. 1A) to a position outside the patient once the assembly is deployed. In other embodiments, the endovascular prosthesis 100 may be deployed without guidewires in the ducts (130 of FIG. 1A) and one or more guidewires advanced into one or more distal openings, such as 134*a*, after the endovascular prothesis 100 is deployed. In some embodiments, a radiopaque marker can be disposed adjacent one or more distal openings, such as 134*a*, to facilitate access of the ducts (130 of FIG. 1A) with one or more guidewires using fluoroscopy.

Whether an elongate medical instrument 170 is thus positioned within a duct 134*a* prior to deployment or after, the elongate medical instrument 170 may be utilized to transition the duct from a closed configuration to an open configuration. This may be done by advancing the elongate medical instrument 170 through the lumen 135*a* and against the closed proximal end 131*a*. An end of the elongate medical instrument 170 may apply a proximally directed force to the closed proximal end 131*a* to selectively open the proximal end 131*a* and the lumen 135*a*. In some embodiments, a medical instrument capable of cutting the closed proximal end 131*a* may be used to form a slit. In another embodiment, the proximal end 131*a* may be selectively opened prior to deployment of the endovascular prosthesis 100 within the vessel. For example, a balloon catheter may be utilized to open the proximal end 131*a* prior to deployment. FIG. 4B shows the elongate medical instrument 170 disposed fully through the duct 130*a*. The intermediate state, wherein the elongate medical instrument is disposed within the duct 130*a* but not fully advanced is thus similar to the configuration of FIG. 4B, though the end of the elongate medical instrument shown proximal of the endovascular prothesis 100 would be disposed at a point along the middle portion (133 of FIG. 3G) of the duct 130. Thus, in some embodiments, upon deployment of the endovascular prothesis 100 to the configuration shown in FIG. 4A, elongate medical instruments, such as 170 of FIG. 4B, may extend from middle portions (133 of FIG. 3G) of each duct 130 to a position outside of the patient. These elongate medical instruments could then be advanced to transition the corresponding duct 130 to an open configuration, or withdrawn to leave the duct 130 in a closed configuration. Thus, each duct 130 may be selectively opened for use, or left in a closed configuration, by a practitioner during treatment allowing the endovascular prosthesis 100 to be patient specific configurable and reducing variations of the endovascular prosthesis 100 needed to treat patients. In certain instances, the endovascular prosthesis 100 may be deployed in a vessel without side branches and each duct 130 is left in the closed configuration such that the endovascular prosthesis 100 functions as a non-fenestrated vascular stent.

When the duct 130*a* is in the opened configuration, blood is allowed to flow through the duct 130*a* and out of the distal opening 134*a* into the diseased section 106. In the configuration of FIG. 4B, duct 130*a* is open while ducts 130*b*, 130*c* remain in a closed configuration. In some embodiments, a medical instrument including an expandable balloon may be disposed within the duct 130*a* and the balloon expanded to open the proximal end 131*a* and the lumen 135*a*. In such embodiments the balloon may be advanced along a guidewire which was prepositioned with the duct 130 prior to deployment or along a guidewire advanced into the duct 130 during the treatment procedure.

The elongate medical instrument 170 may be further advanced proximally to a proximal vascular access site. That is, the elongate medical instrument 170 may be advanced through the duct 130, out of the proximal end of the endovascular prosthesis, and through the vasculature such that it exits the patient's body at a proximal vascular access site. In such instances, the elongate medical instrument can then be used to advance other therapies, such as an expandable tubular prosthesis (171*a* of FIG. 4C) from the proximal vascular access site to the duct 130. In other embodiments the elongate medical instrument 170 may be removed from the vessel 101 through the distal access site.

Figure 4C:
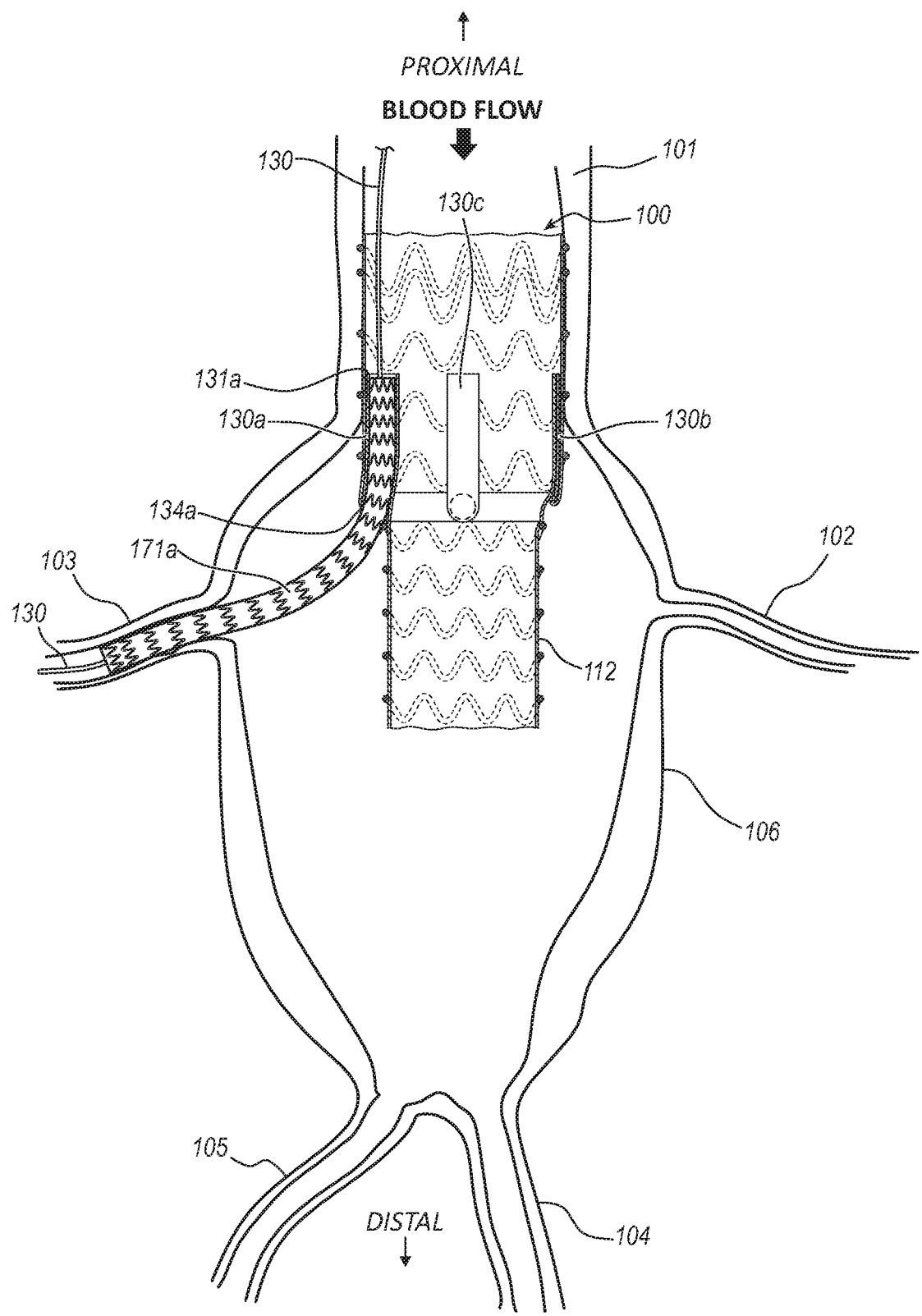
FIG. 4C is a side cross-sectional view of the endovascular prosthesis of FIG. 1A with an expandable tubular prosthesis disposed within the duct and a side branch.

FIG. 4C shows an expandable tubular prosthesis 171*a* sealingly deployed within the duct 130*a*, extending through the distal opening 134*a*, and sealingly deployed into a branch vessel 103. The expandable tubular prosthesis 171*a* may be deployed by advancing a deployment device from the proximal vascular access site along the elongate medical instrument 170. To reach the position shown in FIG. 4C, the elongate medical instrument 170 could be advanced proximally from the position shown in FIG. 4B until the elongate medical instrument 170 exits the body at a proximal vascular access site. This may be done through manipulation of a distal end of the elongate medical instrument 170 disposed outside of the distal vascular access site. The elongate medical device 170 may then be pulled proximally from the proximal end such that the distal end of the elongate medical instrument is pulled into the distal vascular access site, through the vasculature and disposed within or adjacent the duct 130*a*. The elongate medical device 170 may then be advanced via the proximal access site such that the distal end of the elongate medical device 170 advances through the duct 130 and into a branch vessel 103. In such embodiments, both the proximal and distal ends of the elongate medical instrument 170 may be configured with atraumatic ends or ends that can be guided through the anatomy. Embodiments where an elongate medical device is first introduced at the proximal vascular access site and advanced through the previously opened proximal end 131*a*, through the duct 130*a*, through the distal opening 134*a*, and into the branch vessel 103 are also within the scope of this disclosure.

Once a guidewire or similar elongate medical instrument (such as 170 of FIG. 4C) is positioned through the duct 130*a* and into a branch vessel 103, an expandable tubular prosthesis 171*a* may be advanced from the proximal access site (for example in a crimped configuration within a deployment device) and deployed to bridge between the duct 130*a* and the branch vessel 103. The expandable tubular prosthesis 171*a* may be deployed using any suitable deployment instrument (not shown). The expandable tubular prosthesis 171*a* may be configured to be expanded by a balloon or may be self-expanding. Again, the deployment instrument may be inserted over the elongate medical instrument 170 from the proximal access site until the expandable tubular prosthesis 171*a* is appropriately positioned within the duct 130*a* and the branch vessel 103. In the position shown in FIG. 4A, a proximal end of the expandable tubular prosthesis 171*a* is disposed adjacent the proximal end 131*a* of the duct 130*a*. In other embodiments, the proximal end of the expandable tubular prosthesis 171*a* may be disposed distal to the proximal end 131*a* of the duct 130*a*. In still other embodiments, the proximal end of the expandable tubular prosthesis 171*a* may be disposed proximal to the proximal end 131*a* of the duct 130*a*. When positioned as shown in FIG. 4C, the expandable tubular prosthesis 171*a* is deployed to couple the duct 130*a* and the branch vessel 103 such that blood may flow through the expandable tubular prosthesis 171*a* and the branch vessel 103.

Figure 4D:
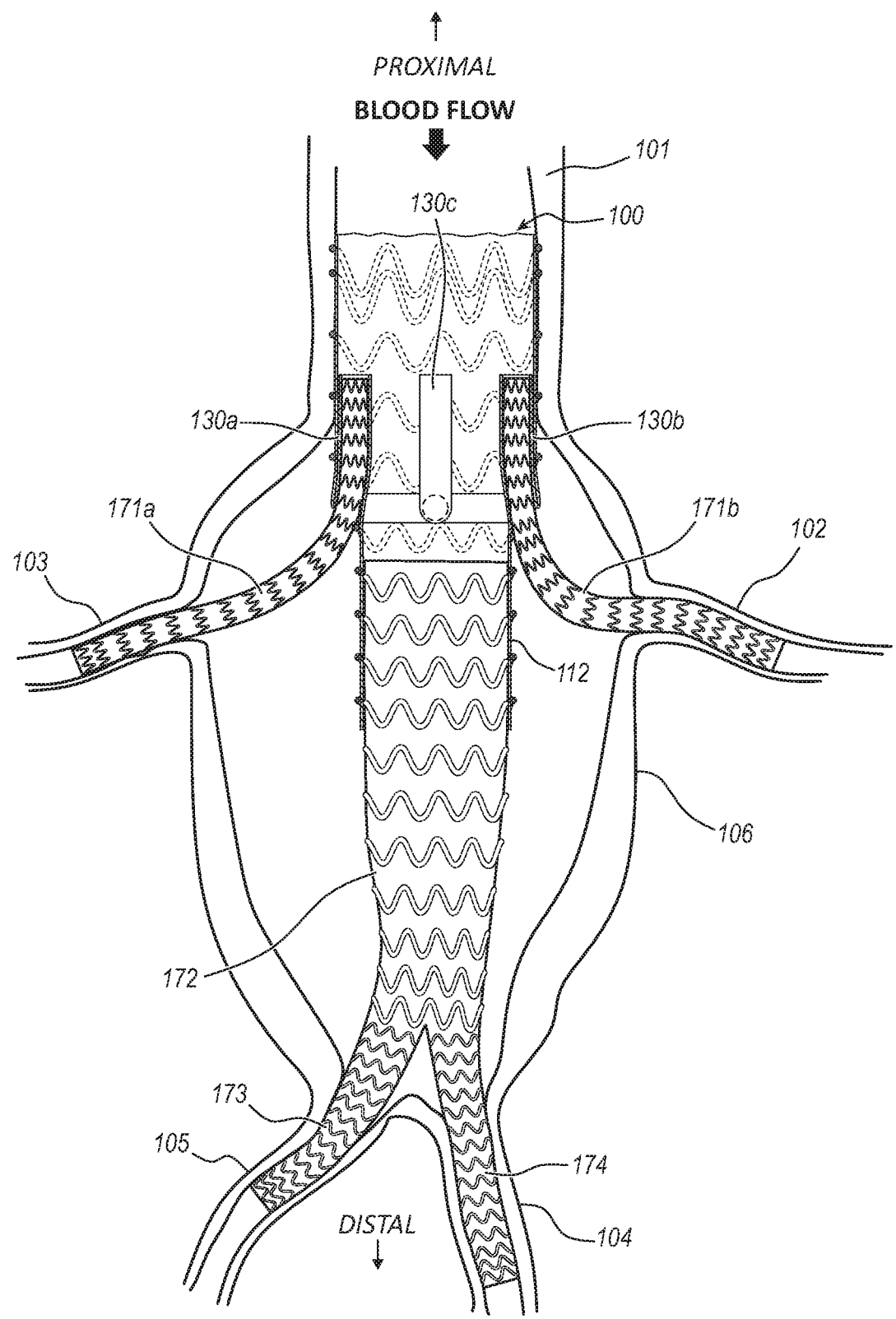
FIG. 4D is a side cross-sectional view of the endovascular prosthesis of FIG. 1A with another expandable tubular prosthesis disposed within another duct and another side branch and another endovascular prosthesis.
Figure 6A:
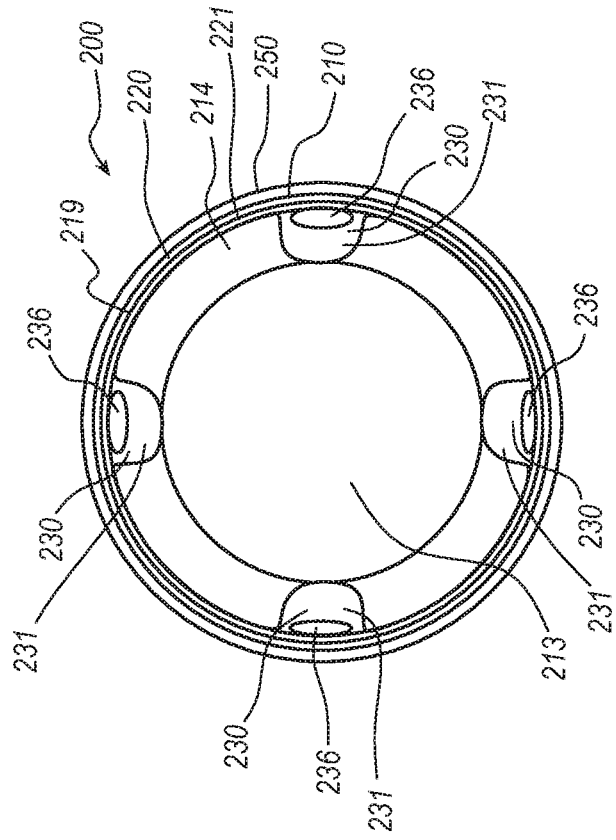
FIG. 6A is a top view of the endovascular prosthesis of FIG. 5A with ducts in a closed configuration.
Figure 6B:
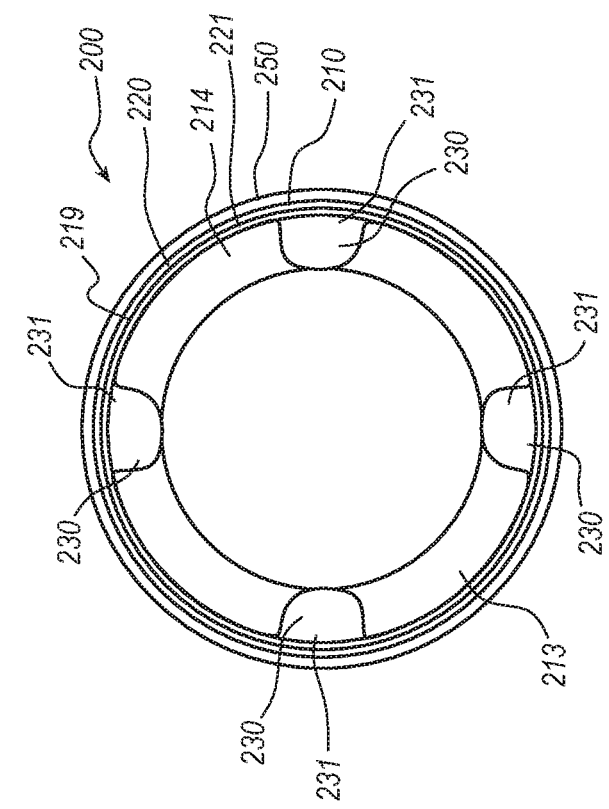
FIG. 6B is a top view of the endovascular prosthesis of FIG. 5A with ducts in an opened configuration.

As shown in FIG. 4D, an analogous procedure may be followed to deploy a second expandable tubular prosthesis 171*b* such that it is sealingly disposed within a second duct 130*b* following selective opening of the duct 130*b* in a similar manner to the opening of the duct 130*a*.

FIGS. 5A-7H depict an embodiment of an endovascular prosthesis 200 that resembles the endovascular prosthesis 100 described above in certain respects. Accordingly, like features are designated with like reference numerals, with the leading digit incremented to "2." For example, the embodiment depicted in FIGS. 5A-7H includes a tubular body 210 that may, in some respects, resemble the tubular body 110 of FIG. 1A. Relevant disclosure set forth above regarding similarly identified features thus may not be repeated hereafter. Moreover, specific features of the endovascular prosthesis 100 and related components shown in FIGS. 1A-4D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the endovascular prosthesis 200 and related components depicted in FIGS. 5A-7H. Any suitable combination of the features, and variations of the same, described with respect to the endovascular prosthesis 100 and related components illustrated in FIGS. 1A-4D can be employed with the endovascular prosthesis 200 and related components of FIGS. 5A-7H, and vice versa. This pattern of disclosure applies equally to further embodiments depicted in subsequent figures and described hereafter, wherein the leading digits may be further incremented.

FIGS. 5A-6B depict an embodiment of an endovascular prosthesis 200. In the illustrated embodiment, the endovascular prosthesis 200 is partially composed of a tubular body 210 and a wire scaffold, framework, or stent, such as wire stent 250. The tubular body 210 may be generally cylindrical in shape having a proximal portion 211, a distal portion 212, a tapered portion 214, and a bore 213.

In the illustrated embodiment, the tubular body 210 includes a plurality of ducts 230. In various embodiments, the tubular body 210 may include one, two, three, four, or more ducts 230. The tubular body 210 and the duct 230 may be formed to be an integral or unibody component such that there is not a seam or joint at a junction of the tubular body 210 and the duct 230. The duct 230 may be disposed within a wall 219 of the tubular body 210 between an inner layer 221 and an outer layer 220 of material. In other words, the inner layer 221 and the outer layer 220 forms a wall of a lumen 235 of the duct 230. Each duct 230 may be oriented such that it extends in a longitudinal orientation parallel to a longitudinal axis 216 and within the wall 219. The duct 230 includes a proximal end 231, a distal end 232, a distal opening 234, and the lumen 235. The duct 230 may be cylindrical in shape. In other embodiments, the duct 230 may include any suitable transverse cross-sectional shape, such as oval, obround, semicircular, D-shaped, flat, etc.

In the illustrated embodiment, the distal opening 234 of the duct 230 is disposed on the tapered portion 214. Positioning the distal opening 234 of any one, or all, of the ducts 230 along other portions of the tubular body 110 is also within the scope of this disclosure. In the illustrated embodiment, the distal opening 234 of each duct 230 is in fluid communication with the lumen 235 of the corresponding duct 230 and with an exterior environment of the endovascular prosthesis 200.

In the illustrated embodiment, for each duct 230, the distal opening 234 is in fluid communication with the corresponding lumen 235. The lumen 235 extends from the distal opening 234 to the proximal end 231 of the lumen 235. Each lumen 235 and proximal opening 236 may be configured to be selectively disposed in a closed configuration or an opened configuration. The lumen 235 and the proximal end 231 for each duct 230 are shown in closed configurations in FIGS. 5A, 5B, and 6A and in opened configurations in FIG. 6B. When in the opened configuration, each of the ducts 230 includes a proximal opening 236. As detailed below, during use some of the lumens 235 and proximal ends 231 may be disposed in the opened configuration while others are in the closed configuration. In certain embodiments, the proximal opening 236 can be formed by cutting the proximal end 231 with a cutting medical instrument, such as a knife, scissors, laser, sonic knife, etc. In other embodiments, the proximal opening 236 may be formed by puncturing the proximal end with a wire or a needle and then dilating the puncture hole.

For each duct 230 and lumen 235 of the illustrated embodiment, in the closed configuration the proximal end 231 and the lumen 235 are selectively closed. The proximal end 231 may be selectively closed by the inner layer 221. In the closed configuration, the duct 230 may be radially compressed such that the duct 230 may not extend into the bore 213 or such that the duct 230 assumes a low-profile configuration along the wall of the bore 213. In the opened configuration, the duct 230 may extend into the bore 213 and allow blood to flow through the duct 230.

In the illustrated embodiment of FIGS. 5A and 5B, the wire scaffolding, framework, or stent such as wire stent 250 is shown to circumferentially surround the tubular body 210. The wire stent 250 may be configured to radially expand the tubular body 210 from a crimped or delivery configuration to a deployed configuration. When the endovascular prosthesis 200 is deployed within a blood vessel, the tubular body 210 may be pressed against a wall of the blood vessel. The wire stent 250 may be formed of any suitable material, such as nickel-titanium alloy, stainless steel, platinum, polymers, etc. The wire stent 250 may have a zig-zag pattern, a wave pattern, or any other suitable pattern. The wire stent 250 may be pre-formed or formed over the tubular body 210. The material, pattern, and wire diameter of the wire stent 150 may be configured to provide a chronic radial outwardly directed force and a resistance to a radial inwardly directed force.

Figure 7E:
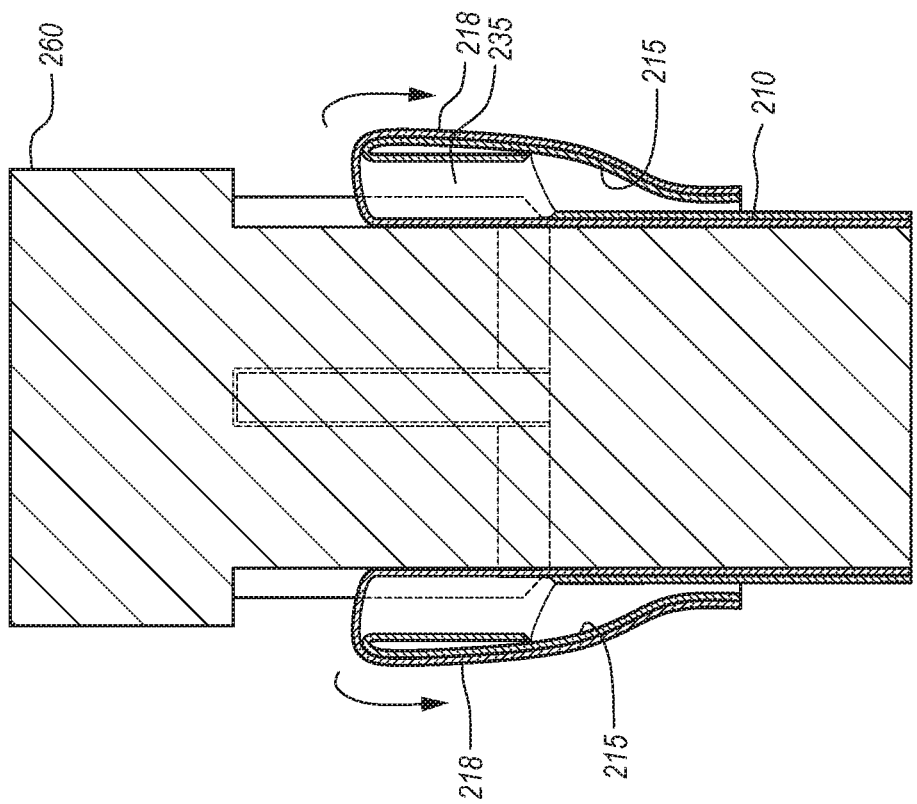
FIG. 7E is a cross-sectional view of the tubular body of the endovascular prosthesis of FIG. 5A in a pre-inverted state.

FIGS. 7A-7H illustrate a method of manufacturing the endovascular prosthesis 200. FIG. 7A depicts a body forming mandrel 260. The body forming mandrel 260 may include a proximal portion 261, a distal portion 262, a tapered portion 263, and a plurality of duct forming grooves or troughs 267. The body forming mandrel 260 may be generally cylindrical in shape and formed from any suitable material, such as stainless steel, aluminum, etc. As depicted in FIG. 7B, the body forming mandrel 260 may have a solid transverse cross-section. In other embodiments, the body forming mandrel 260 may include a bore extending through the body forming mandrel 260. The dimensions (e.g., lengths, diameters, angle) of the body forming mandrel 260 may correspond to the dimensions of the tubular body 210 previously described.

In various embodiments, the body forming mandrel 260 may include one, two, three, four, or more duct forming grooves or troughs 267. In the illustrated embodiment, each duct forming groove 267 is shown to extend radially into the body forming mandrel 260 parallel to a longitudinal axis 264 of the body forming mandrel 260. The duct forming grooves 267 may be sized and shaped to receive a duct forming mandrel 266 as will be discussed below. In another embodiment, the body forming mandrel 260 comprises a smooth outer surface.

FIG. 7B depicts the body forming mandrel 260 and the duct forming grooves 267 covered with the outer layer 220 of material. The material of the outer layer 220 may be comprised of any of the materials of the tubular body 210 discussed above. The outer layer 220 may be applied using any suitable technique. For example, the outer layer 220 may be applied by wrapping strips of material around the body forming mandrel 260, dipping the body forming mandrel 260 into a solution of material and solvent, spraying the body forming mandrel 260 with a solution of material and solvent, etc. In some embodiments, the outer layer 220 may include multiple sub-layers of either the same material or different materials.

FIG. 7C depicts duct forming mandrels 266 disposed in the duct forming troughs 267 such that the inner layer 220 is disposed between the duct forming mandrel 266 and the duct forming trough 267. In certain embodiments, the duct forming mandrel 266 may be disposed on a smooth surface of the body forming mandrel 260. Diameter and length dimensions of each duct forming mandrel 266 may be approximately equivalent to the dimensions of the ducts 230 previously described. The duct forming mandrels 266 may be formed from the same material as the body forming mandrel 260 or may comprise other materials. The duct forming mandrel 266 may have any suitable transverse cross-sectional shape to match a desired shape of the ducts 230. For example, the transverse cross-sectional shape may be circular, oval, obround, semicircular, D-shaped, etc.

In some embodiments, the duct forming mandrel 266 may be a strip of a film of a material, such as polyimide or any other suitable material. A width of the strip may be sized to form the duct 230 having an inner diameter as previously discussed. In other embodiments, the strip may be wrapped with a reinforcing film, positioned on the body forming mandrel 260 to form a lining for the duct 230.

FIG. 7D depicts an inner layer 221 of material covering the body forming mandrel 260, the duct forming mandrels 266, and the outer layer 220. The material of the inner layer 221 may be comprised of any of the materials of the tubular body 210 discussed above and may be the same or different than the material of the outer layer 220. The inner layer 221 may be applied using any suitable technique. For example, the inner layer 221 may be applied by wrapping strips of material around the body forming mandrel 260, dipping the body forming mandrel 260 into a solution of material and solvent, spraying the body forming mandrel 260 with a solution of material and solvent, etc. In some embodiments, the inner layer 221 may include multiple sub-layers of either the same material or different materials. The outer layer 220 and the inner layer 221 may be cured and/or sintered prior to removal from the body forming mandrel 260 to set and fuse the materials. The curing and/or sintering parameters may include heat, moisture, ultraviolet radiation, etc. and may be dependent upon the material of the layers 220, 221.

FIG. 7E shows the tubular body 210 in a pre-inverted state prior to the tubular body 210 being removed from the body forming mandrel 260. The duct mandrels 266 are removed from the duct lumens 235 and distal openings 234. As shown in FIG. 7E, the material that will be an interior surface 215 of the tubular body 210 is on the outside and the material that will be the exterior surface 218 of the tubular body 210 is in contact with the body forming mandrel 260. The ducts 230 are extending radially outward from the tubular body 210. In other words, the layers 220, 221 may be applied to the body forming mandrel 260 with the layers 220, 221 being inverted after application to form the endovascular prosthesis 200.

In other embodiments, the tubular body 210 is not inverted as it is removed from the body forming mandrel 260. In such embodiments, the tubular body 210 may be longitudinally slid off of the body forming mandrel 260 such that the inner surface 215 remains on the exterior of the tubular body 210 and the exterior 218 remains on the interior of the tubular body 210. In such embodiments, the tubular body 210 may thus be configured for use without ever inverting the tubular body 210 as part of the manufacturing process. Procedures wherein the tubular body 210 is not inverted may contain any of the other steps related above in connection with manufacturing processes wherein the tubular body 210 is inverted as part of the manufacturing process.

Figure 7F:
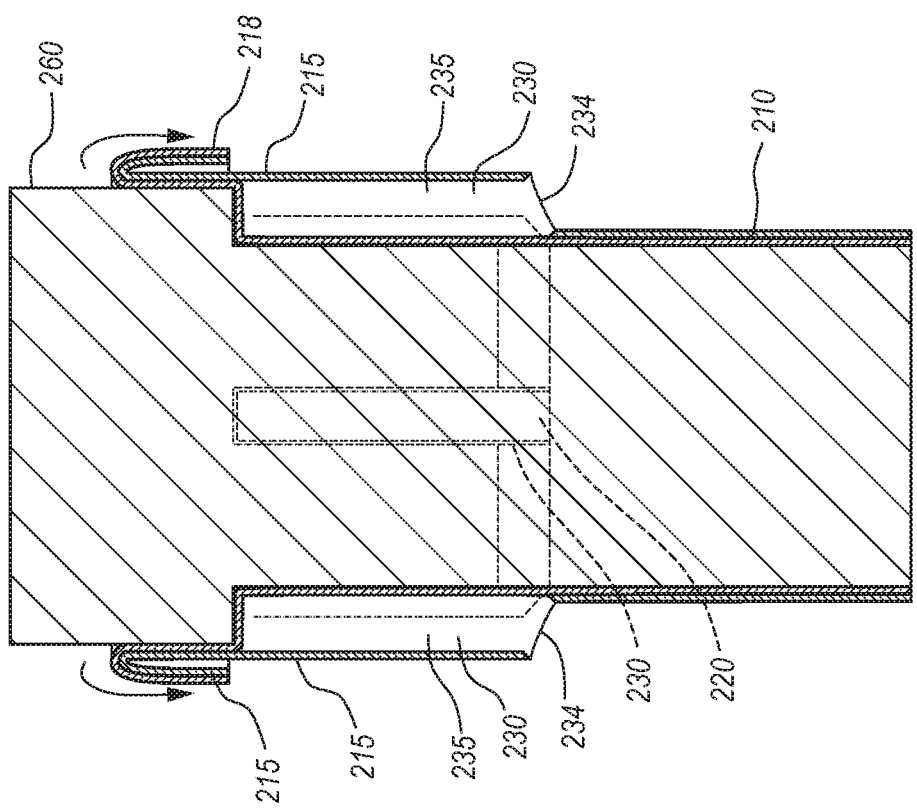
FIG. 7F is a cross-sectional view of the tubular body of the endovascular prosthesis of FIG. 5A in a partial inverted state.

FIG. 7F shows the tubular body 210 of FIG. 7E partially removed from the body forming mandrel 260 and partially inverted such that a portion of the interior surface 215 is on the inside of the tubular body 210 and a portion of the exterior surface 218 is on the outside of the tubular body 210.

Figure 7H:
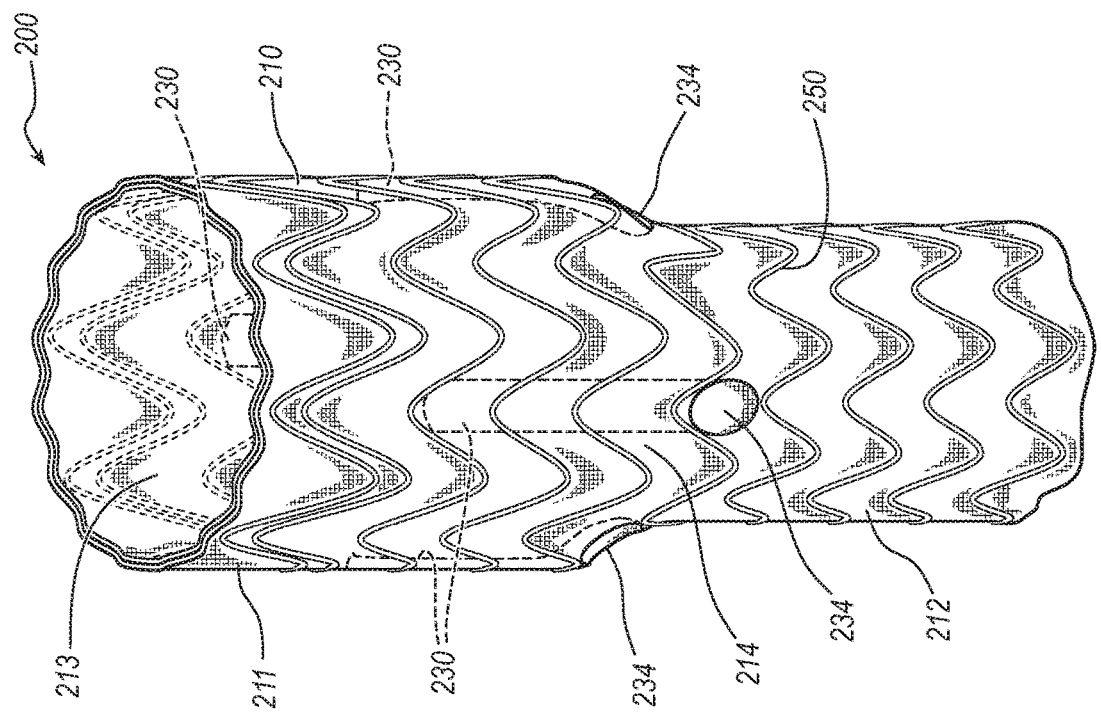
FIG. 7H is another perspective view of the endovascular prosthesis of FIG. 5A.
Figure 7G:
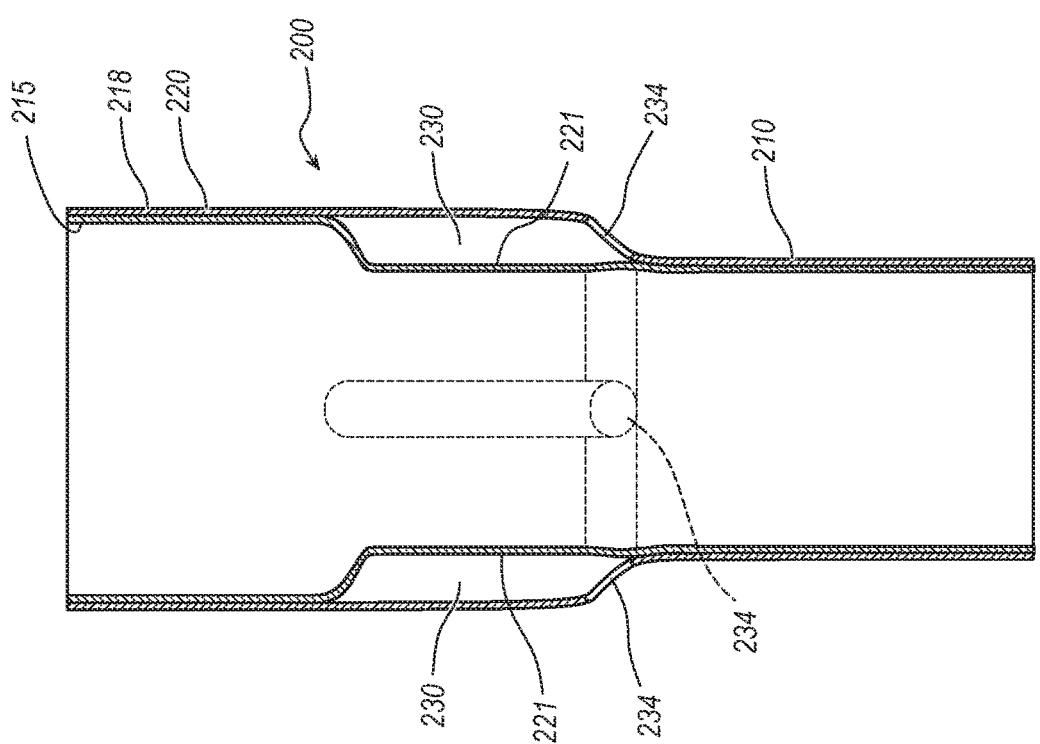
FIG. 7G is a perspective view of the tubular body of the endovascular prosthesis of FIG. 5A in a fully inverted state.

FIG. 7G depicts the tubular body 210 fully inverted where the ducts 230 are disposed between the layers 220, 221 of the tubular body 210 and the distal openings 234 of the ducts 230 are disposed on the outside of the tubular body 210. The proximal ends 231 of the ducts 230 are closed by the inner layer 221. The interior surface 215 is on the inside and the exterior surface 218 is on the outside of the tubular body 210. In other embodiments, the tubular body 210 may be removed from the body forming mandrel 260 without inverting the tubular body 210. In other words, the tubular body 210 may be slid straight off the body forming mandrel 260.

FIG. 7H shows the wire stent 250 surrounding and coupled to the tubular body 210 to complete the manufacturing of the endovascular prosthesis 200. The wire stent 250 may be applied around the tubular body 210 after the tubular body is removed from the mandrel 260 and inverted. The wire stent 250 may be pre-formed on a wire bending mandrel prior to placement over the tubular body 210. In another embodiment, the wire stent 250 may be wound around the tubular body 210. The wire stent 250 may be coupled to the tubular body 210 using any suitable technique. For example, the wire stent 250 may be coupled to the tubular body 210 using an adhesive, suture stitches, clips, staples, tapes, films, membranes, etc. In some embodiments, the wire stent 250 may be captured between layers of the materials of the tubular body 210. For example, a first layer of material can be applied to the body forming mandrel 260, the wire stent 250 positioned over the first layer, and then a second layer of material applied over the wire stent 250.

Methods within the scope of this disclosure may comprise use of endovascular prosthesis 200 with any number of ducts 230. Depending on the nature of the diseased vessel, all the ducts 230 may be opened and utilized or any subset thereof. Thus, endovascular prothesis 200 within the scope of this disclosure may be configured such that any number of ducts 230 within a plurality of ducts 230 may be selectively opened and coupled to a branch vessel and any number may remain in a closed configuration. Endovascular protheses within the scope of this disclosure may be configured for indefinite use and implantation with a subset of the plurality of ducts 230 in an open configuration and a subset of the plurality of ducts 230 in a closed configuration.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A vascular prosthesis, comprising:
 a body, comprising a proximal portion, a tapered portion, a distal portion, and one or more bores;
 wherein the tapered portion is between the proximal portion and the distal portion, extends around a circumference of the body, and a diameter of the proximal portion is larger than a diameter of the distal portion; and
 a duct extending along at least a portion of a length of a wall of each of the one or more bores, the duct comprising:
  a proximal end, a distal end, a lumen extending between the proximal end and the distal end, and a distal opening disposed adjacent the distal end,
  wherein the distal opening is disposed within a wall of the tapered portion of the body, wherein the distal opening is in fluid communication with the lumen,
  wherein the proximal end is configured to be selectively openable from a closed configuration to an opened configuration, and wherein the lumen has a length between 5 mm and 50 mm.

2. The vascular prosthesis of claim 1, wherein the duct proximal end is configured to be selectively transitioned from the closed configuration to the opened configuration when a distally directed axial force is applied by an elongate medical device.

3. The vascular prosthesis of claim 1, wherein the lumen is configured to be selectively transitioned from a closed configuration to an opened configuration.

4. The vascular prosthesis of claim 1, wherein the duct lumen is configured to sealingly receive an expandable tubular prosthesis when in the opened configuration.

5. The vascular prosthesis of claim 1, further comprising a wire stent coupled to the body.

6. The vascular prosthesis of claim 1, wherein the duct is disposed within the wall of the body.

7. The vascular prosthesis of claim 1,
 wherein the wall of the body comprises a first layer of material and a second layer of material; and
 wherein the duct is disposed between the first layer and the second layer.

8. A vascular prosthesis, comprising:
 a body, comprising a proximal portion, a distal portion, and one or more bores; and
 a plurality of ducts extending along at least a portion of a length of a wall of each of the one or more bores, each duct of the plurality of ducts comprising:
  a proximal end, a distal end, a lumen extending between the proximal end and the distal end, and a distal opening disposed adjacent the distal end,
  wherein the distal opening and the duct comprise a continuous construction with a wall of the body, wherein the distal opening is in fluid communication with the lumen, and wherein the proximal end is configured to be selectively openable from a closed configuration to an opened configuration.

9. A vascular prosthesis, comprising:

a body, comprising a proximal portion, a tapered portion, a distal portion, and one or more bores;

wherein the tapered portion is between the proximal portion and the distal portion, extends around a circumference of the body, and a diameter of the proximal portion is larger than a diameter of the distal portion; and a plurality of ducts extending along at least a portion of a length of a wall of each of the one or more bores, each duct of the plurality of ducts comprising:

a proximal end, a distal end, a lumen extending between the proximal end and the distal end, and a distal opening disposed adjacent the distal end, wherein the distal opening is disposed within a wall of the tapered portion of the body, wherein the distal opening is in fluid communication with the lumen, wherein the proximal end is configured to be selectively openable from a closed configuration to an opened configuration, and wherein the wall of the duct has a thickness between 0.07 mm and 0.5 mm.

* * * * *